(12) United States Patent
Liang et al.

(10) Patent No.: US 7,817,824 B2
(45) Date of Patent: Oct. 19, 2010

(54) UNIFIED SYSTEM AND METHOD FOR ANIMAL BEHAVIOR CHARACTERIZATION FROM TOP VIEW USING VIDEO ANALYSIS

(75) Inventors: Yiqing Liang, Vienna, VA (US);
Vikrant Kobla, Ashburn, VA (US);
Xuesheng Bai, Ashburn, VA (US); Yi Zhang, Baltimore, MD (US); Linda S Crnic, Denver, CO (US); Stan L. Wilks, legal representative, Denver, CO (US);
Wayne Wolf, Atlanta, GA (US)

(73) Assignee: Clever Sys, Inc., Reston, VA (US)

( * ) Notice: Subject to any disclaimer, the term of this patent is extended or adjusted under 35 U.S.C. 154(b) by 87 days.

(21) Appl. No.: 12/365,149

(22) Filed: Feb. 3, 2009

(65) Prior Publication Data
US 2009/0296992 A1    Dec. 3, 2009

Related U.S. Application Data

(63) Continuation of application No. 10/698,008, filed on Oct. 30, 2003, now abandoned, which is a continuation-in-part of application No. 09/718,374, filed on Nov. 24, 2000, now Pat. No. 6,678,413.

(51) Int. Cl.
*G06K 9/00* (2006.01)
*G06K 9/34* (2006.01)
*G06K 9/48* (2006.01)
*G06K 9/36* (2006.01)
*G06K 9/40* (2006.01)
*A61K 49/00* (2006.01)
*H04N 1/46* (2006.01)

(52) U.S. Cl. .................. 382/110; 382/173; 382/199; 382/266; 382/291; 358/538; 424/9.1

(58) Field of Classification Search ............... 382/110
See application file for complete search history.

(56) References Cited

U.S. PATENT DOCUMENTS 3,100,473 A    8/1963    Kissel (Continued)

FOREIGN PATENT DOCUMENTS

EP    363755 A2    4/1990

(Continued)

OTHER PUBLICATIONS

AccuScan on-line catalog, Nov. 19, 1997.

(Continued)

*Primary Examiner*—Anand Bhatnagar
*Assistant Examiner*—Jose M Torres
(74) *Attorney, Agent, or Firm*—Alston & Bird LLP

(57) ABSTRACT

In general, the present invention is directed to systems and methods for finding the position and shape of an animal using video. The invention includes a system with a video camera coupled to a computer in which the computer is configured to automatically provide animal segmentation and identification, animal motion tracking (for moving animals), animal feature points and segments identification, and behavior identification. In a preferred embodiment, the present invention may use background subtraction for animal identification and tracking, and a combination of decision tree classification and rule-based classification for feature points and segments and behavior identification. Thus, the present invention is capable of automatically monitoring a video image to identify, track and classify the actions of various animals and the animal's movements within the image. The image may be provided in real time or from storage. The invention is particularly useful for monitoring and classifying animal behavior for testing drugs and genetic mutations, but may be used in any of a number of other surveillance applications.

41 Claims, 9 Drawing Sheets

U.S. PATENT DOCUMENTS

| | | | |
|---|---|---|---|
| 3,304,911 | A | 2/1967 | Hakata et al. |
| 3,485,213 | A | 12/1969 | Scanlon |
| 3,803,571 | A | 4/1974 | Luz |
| 3,974,798 | A | 8/1976 | Meetze, Jr. |
| 4,337,726 | A | 7/1982 | CzekaJewski et al. |
| 4,517,593 | A | 5/1985 | Keller et al. |
| 4,574,734 | A | 3/1986 | Mandalaywala et al. |
| 4,600,016 | A | 7/1986 | Boyd et al. |
| 4,631,676 | A | 12/1986 | Pugh |
| 4,888,703 | A | 12/1989 | Baba et al. |
| 5,299,454 | A | 4/1994 | Fuglewicz et al. |
| 5,428,723 | A | 6/1995 | Ainscow et al. |
| 5,546,439 | A | 8/1996 | Hsieh |
| 5,581,276 | A | 12/1996 | Cipolla et al. |
| 5,596,994 | A | 1/1997 | Bro |
| 5,708,767 | A | 1/1998 | Yeo et al. |
| 5,748,775 | A | 5/1998 | Tsuchikawa et al. |
| 5,816,256 | A | 10/1998 | Kissinger et al. |
| 5,821,945 | A | 10/1998 | Yeo et al. |
| 5,870,138 | A | 2/1999 | Smith et al. |
| 6,010,465 | A | 1/2000 | Nashner |
| 6,061,088 | A | 5/2000 | Khosravi et al. |
| 6,072,496 | A | 6/2000 | Guenter et al. |
| 6,072,903 | A | 6/2000 | Maki et al. |
| 6,081,607 | A | 6/2000 | Mori et al. |
| 6,088,468 | A | 7/2000 | Ito et al. |
| 6,144,366 | A | 11/2000 | Numazaki et al. |
| 6,212,510 | B1 | 4/2001 | Brand |
| 6,231,527 | B1 | 5/2001 | Sol |
| 6,242,456 | B1 | 6/2001 | Shuster et al. |
| 6,263,088 | B1 | 7/2001 | Crabtree et al. |
| 6,295,367 | B1 | 9/2001 | Crabtree et al. |
| 6,311,644 | B1 | 11/2001 | Pugh |
| 6,334,187 | B1 | 12/2001 | Kadono |
| 6,456,737 | B1 | 9/2002 | Woodfill et al. |
| 6,468,998 | B1 | 10/2002 | Kuroita et al. |
| 6,535,131 | B1 | 3/2003 | Bar-Shalom et al. |
| 6,576,237 | B1 | 6/2003 | Ingham et al. |
| 6,601,010 | B1 | 7/2003 | Fowler et al. |
| 6,630,148 | B1 | 10/2003 | Ingham et al. |
| 6,630,347 | B1 | 10/2003 | Huang et al. |
| 6,650,778 | B1 | 11/2003 | Matsugu et al. |
| 6,678,413 | B1 | 1/2004 | Liang et al. |
| 6,704,502 | B2 | 3/2004 | Morofuji |
| 6,715,444 | B1 | 4/2004 | Yabusaki et al. |
| 6,757,444 | B2 | 6/2004 | Matsugu et al. |
| 6,819,796 | B2 | 11/2004 | Hong et al. |
| 6,837,184 | B2 | 1/2005 | Gondhalekar et al. |
| 6,899,686 | B2 | 5/2005 | Hampton et al. |
| 6,941,239 | B2 | 9/2005 | Unuma et al. |
| 7,133,537 | B1 | 11/2006 | Reid |
| 7,269,516 | B2 | 9/2007 | Brunner et al. |
| 2003/0024482 | A1 | 2/2003 | Gondhalekar et al. |
| 2003/0100998 | A2 | 5/2003 | Brunner et al. |
| 2004/0009845 | A1 | 1/2004 | Johnson |
| 2004/0020443 | A1 | 2/2004 | Ohl |
| 2004/0141635 | A1 | 7/2004 | Liang et al. |
| 2004/0141636 | A1 | 7/2004 | Liang et al. |

FOREIGN PATENT DOCUMENTS

| | | |
|---|---|---|
| JP | 63-1 33061 | 6/1988 |
| JP | 08-063603 | 3/1996 |
| JP | 08-240830 | 9/1996 |
| JP | 09-073541 | 3/1997 |
| JP | 09-251441 | 9/1997 |
| JP | 11-052215 | 2/1999 |
| JP | 11-259643 | 9/1999 |
| JP | 11-296651 | 10/1999 |
| JP | 2000-215319 | 8/2000 |
| WO | WO/02/43352 | 5/2002 |

OTHER PUBLICATIONS

Allen, William H. "Animals and their Models do their Locomotions: Biologists Probe Mechanics and Energetics of Animal Motion". Jun. 1995. Biosciences. vol. 45, No. 6, pp. 381-383.

Automated Plus Maze Open/Closed Arm System; AccuScan Instruments, Inc., 1991.

Birch et al. 2001. "A miniature Hybrid Robot Propelled by Legs". Proceedings of the 2001 IEE/RSJ International Conference on Intelligent Robots and Systems, p. 845-851.

Clarke, K.A. and J. Still "Development and consistency of gait in the mouse" Physiology & Behavior 73:159-164 (2001).

Clarke, K.A. and J. Still "Gait Analysis in the Mouse" Physiology & Behavior 66(5):723-729 (1999).

Cohen, J.J. et al.; "Behavior, Stress, and Lymphocyte Recirculation"; Stress, Immunity and Aging; 1984; pp. 73-80.

Coussons-Read, Mary E. et al.; "Behavioral Assessment of the Ts65Dn Mouse, A Model for Down Syndrome: Altered Behavior in the Elevated Plus Maze and Open Field"; Behavior Genetics; vol. 26; No. 1; 1996; pp. 7-13.

Crnic, L.S. et al.; "Animal Models of Mental Retardation: An Overview"; Mental Retardation and Developmental Disabilities Research Reviews; vol. 2; 1996; pp. 185-187.

Crnic, L.S. et al.; "Animal Modes of Human Behavior: Their Application to the Study of Attachment"; The Development of Attachment and Affiliative Systems: Neurobiological and Psychobiological Aspects, Plenum, New York; 1982; pp. 31-42.

Crnic, L.S. et al.; "Behavioral Effects of Mouse Interferons-α and -γ and Human Interferon-.alpha. In Mice"; Brain Research; vol. 590; 1992; pp. 277-284.

Crnic, L.S. et al.; "Behavioral Effects of Neonatal Herpes Simplex Type 1 Infection of Mice"; Neurotoxicology and Teratology; vol. 10; 1988; pp. 381-386.

Crnic, L.S. et al.; "Down Syndrome: Neuropsychology and Animal Models"; Progress in Infancy Research; vol. 1; 2000; pp. 69-111.

Crnic, L.S. et al.; "Prostaglandins Do Not Mediate Interferon-.alpha. Effects on Mouse Behavior"; Physiology & Behavior; vol. 51; 1992; pp. 349-352.

Crnic, L.S. et al.; "Separation-Induced Early Malnutrition: Maternal, Physiological and Behavioral Effects"; Physiology & Behavior; vol. 26; 1981; pp. 695-706.

Crnic, L.S.; "Animal Models of Early Malnutrition: A Comment on Bias, Dependability, and Human Importance"; Malnutrition and Behavior: Critical Assessment of Key Issues; 1984; pp. 460-468.

Crnic, L.S.; "Behavioral Consequences of Virus Infection"; Psychoneuroimmunology, Second Edition; Academic Press; 1991; pp. 749-769.

Crnic, L.S.; "Early Experience Effects: Evidence for Continuity?"; Continuities and Discontinuities in Development, Plenum Press, New York; 1984; pp. 355-368.

Crnic, L.S.; "Effects of Infantile Undernutrition on Adult Learning in Rats: Methodological and Design Problems"; Psychological Bullentin; vol. 83; No. 4; 1976; pp. 715-728.

Crnic, L.S.; "Effects of Infantile Undernutrition on Adult Sucrose Solution Consumption in the Rat"; Physiology & Behavior; vol. 22; 1979; pp. 1025-1028.

Crnic, L.S.; "Effects of Nutrition and Environment on Brain Biochemistry and Behavior"; Developmental Psychobiology; vol. 16; 1983; pp. 129-145.

Crnic, L.S.; "Maternal Behavior in the Undernourished Rats (*Rattus norvegicus*)"; Physiology & Behavior; vol. 16; 1976; pp. 677-680.

Crnic, L.S.; "Models of Infantile Malnutrition in Rats: Effects on Maternal Behavior"; Developmental Psychobiology; vol. 13; 1980; pp. 615-628.

Crnic, L.S.; "Nutrition and Mental Development"; American Journal of Mental Deficiency; vol. 88; No. 5; 1984 pp. 526-533.

Crnic, L.S.; "The Effects of Chronic Lithium Chloride Administration on Complex Schedule Performance, Activity, and Water Intake in the Albino Rat"; Physiological Psychology; vol. 4; 1976; pp. 166-170.

Crnic, L.S.; "The Use of Animal Models to Study Effects of Nutrition on Behavior"; Diet and Behavior: A Multidisciplinary Approach; Springer-Verlag; 1990; pp. 73-87.

Crnic, L.S.; "Transgenic and Null Mutant Animals for Psychosomatic Research"; Psychosomatic Medicine; vol. 58; 1996; pp. 622-632.

Crnic, Linda S. et al., "Automated Analysis of Digitized Videotapes of Mouse Home-Cage Behavior", Feb. 17, 2000.

Dierssen, Mara et al.; "Murine Models for Down Syndrome"; Physiology and Behavior; vol. 73; 2001; pp. 859-871.

Digiscan DMicro System; AccuScan Instruments, Inc., 1996.

Digiscan Model CCDIGI Optical Animal Activity Monitoring System, AccuScan Instruments, Inc., 1997.

Digiscan Optical Animal Activity Monitoring System, AccuScan Instruments, Inc., 1997.

Dorai, C. et al.; "Generating Motion Descriptors From MPEG-2 Compressed HDTV Video for Content-Based Annotation and Retrieval"; In Proceedings of IEEE Third Workshop on Multimedia Signal Processing (MMSP); Sep. 1999; (4pgs).

Dorai, C. et al; "Extracting Motion Annotations From MPEG-2 Compressed Video for HDTV Content Management Applications"; IEEE International Conference on Multimedia Computing and Systems; Jun. 1999; (6pgs).

Dunn, Andrea L. et al.; "Repeated Injections of Interferon-α A/D in Balb/c Mice: Behavioral Effects"; Brain, Behavior, and Immunity; vol. 7; 1993; pp. 104-111.

EthoVision, computer vision system for automation of behavioral experiments, Noldus Information Technology, 1997.

Fitzgerald, R.E. et al., "Validation of a Photobeam System for Assessment of Motor Activity in Rats," Toxicology, 49 (1988) pp. 433-439.

Granholm, Ann-Charlotte et al.; "Loss of Cholinergic Phenotype in Basal Forebrain Coincides With Cognitive Decline in a Mouse Model of Down's Syndrome"; Experimental Neurology; vol. 161; 2000; pp. 647-663.

Gurney, Mark E. et al. "Motor Neuron Degeneration in Mice That Express a Human Cu,Zn Superoxide Dismutase Mutation" Science 264:1772-1775 (Jun. 17, 1994).

HVS Image Homepage Nov. 25, 1997; Video tracking system for Morris water maze, open field, radial-arm maze, etc.

Hyde, L.A. et al.; "Age-Related Deficits in Context Discrimination Learning in Ts65Dn Mice That Model Down Syndrome and Alzheimer's Disease"; Behavioral Neuroscience; vol. 115; 2001; pp. 1-8.

Hyde, L.A. et al.; "Motor Learning in Ts65Dn Mice, a Model for Down Syndrome"; Developmental Psychobiology; vol. 38; 2001; pp. 33-45.

Hyde, L.A. et al.; "Ts65Dn Mice, A Model for Down Syndrome, Have Deficits in Context Discrimination Learning Suggesting Impaired Hippocampal Function"; Behavioral Brain Research; vol. 118; 2001; pp. 53-60.

Jones, A.P. et al.; "Maternal Mediation of the Effects of Malnutrition"; The Handbook of Behavioral Teratology; Plenum; 1986; pp. 409-425.

Kobla, Vikrant et al.; "Archiving, Indexing, and Retrieval of Video in the Compressed Domain"; In Proceedings of SPIE Conference on Multimedia Storage and Archiving Systems; vol. 2916; Nov. 1996; (12pgs).

Kobla, Vikrant et al.; "Compressed Domain Video Indexing Techniques Using DCT and Motion Vector Information in MPEG Video"; in Proceedings of SPIE Conference on Storage and Retrieval for Image and Video Databases V; vol. 3022; Feb. 1997; (12pgs).

Kobla, Vikrant et al.; "Compressed Domain Video Segmentation"; CFAR Technical Report CS-TR-3688, University of Maryland, College Park; Oct. 25, 1996; (34pgs).

Kobla, Vikrant et al.; "Detection of Slow-Motion Replay Sequences for Identifying Sports Videos"; In Proceedings of IEEE Third Workshop on Multimedia Signal Processing (MMSP); Sep. 1999; (6pgs).

Kobla, Vikrant et al.; "Developing High-Level Representations of Video Clips Using Video Trails"; In Proceedings of SPIE Conference on Storage and Retrieval for Image and Video Databases VI; Jan. 1998; (12pgs).

Kobla, Vikrant et al.; "Extraction of Features for Indexing MPEG-Compressed Video"; In Proceedings of IEEE First Workshop on Multimedia Signal Processing (MMSP); Jun. 1997; (6pgs).

Kobla, Vikrant et al.; "Feature Normalization for Video Indexing and Retrieval"; CFAR Technical Report CS-TR-3732, University of Maryland, College Park; Nov. 1996; (40pgs).

Kobla, Vikrant et al.; "Identifying Sports Videos Using Replay, Text, and Camera Motion Features"; Proceedings of the SPIE Conference on Storage and Retrieval for Media Databases; vol. 3972; Jan. 2000; (12pgs).

Kobla, Vikrant et al.; "Indexing and Retrieval of MPEG Compressed Video"; Journal of Electronic Imaging; vol. 7(2); Apr. 1998; (36pgs).

Kobla, Vikrant et al.; "Special Effect Edit Detection Using Video Trials: A Comparison With Existing Techniquess"; Proceedings of SSPIE Conference on Storage and Retrieval for Image and Video Databases VII; Jan. 1999; (12pgs).

Kobla, Vikrant et al.; "Video Trails: Representing and Visualizing Structure in Video Sequences"; In Proceedings of ACM Multimedia Conference; Nov. 1997; (12pgs).

Kram, R., Wong, B. and Full, R.J. 1997. "Three-Dimensional Kinematics and Limb Kinetic Energy of Running Cockroaches". The Journal of Experimental Biology 200, 1919-1929.

Li, Yanbing et al; "Semantic Image Retrieval Through Human Subject Segmentation and Characterization"; In Storage and Retrieval for Image and Video Databases V, SPIE; vol. 3022; 1997; pp. 340-351.

Liang Yiqing et al.; "A Ground Target Detection System for Digital Video Database"; Conference on Visual Information Processing VII, AeroSense '98, Orlando, Florida; Apr. 1998; (6pgs).

Liang, Yiqing et al.; "A Practical Video Indexing and Retrieval System"; Applied Imagery and Pattern Recognition (AIPR) '97, Washington, D.C.; Oct. 1997; (8pgs).

Liang, Yiqing et al.; "Apprenticeship Learning of Domain Models"; Seventh Intl. Conference on Software Engineering and Knowledge Engineering, Rockville, Maryland; Jun. 1995; (9pgs).

Liang, Yiqing et al.; "Multiple Motion Detection Using Genetic Algorithms"; DARPA Image Understanding Workshop, Monterey, CA; Nov. 1998; (8pgs).

Liang, Yiqing et al.; "Toward an Object and Multiple-Modalities Based Indexing and Retrieval of Video Contents"; DARPA's Image Understanding Workshop; Monterey, California; Nov. 1998; (21pgs).

Liang, Yiqing et al; "A Practical Video Database Based on Language and Image Analysis"; AAAI Technical Report, SS-97-03,, ed., Alex Hauptmann & Michael Witbrock, Intelligent Use and Integration of Text, Image, Video and Speech; Mar. 1997; (6pgs).

Liang, Yiqing et al; "A Shot Boundary Detection Algorithm Adapted for Predator Video"; Applied Imagery and Pattern Recognition (AIPR) '98; Washington, D.C.; Oct. 1998; (9pgs).

Liang, Yiqing Ph.D.; "Video Retrieval Based on Language and Image Analysis"; Defense Advanced Research Projects Agency Information Systems Office; May 28, 1999; 35 pgs.

Liang, Yiqing; "A Practical Digital Video Database Based on Language and Image Analysis"; International Conference Multimedia Databases on Internet; Seoul, Korea; Oct. 10, 1997; (23pgs).

Liang, Yiqing, "Digital Video Technologies and Their Applications," Beijing Dec. 2000, 24 pages.

Liu, Bede et al.; "The Princeton Video Library of Politics"; Digital Libraries '94, Texas A & M University; Jun. 1994; pp. 215-216.

Macmillan, D.L. "A Physiological Analysis of Walking in the American Lobster". Feb. 6, 1975. Biological Sciences (England) vol. 270.

Nielsen, D.M. et al.; "Elevated Plus Maze Behavior, Auditory Startle Response,, and Shock Sensitivity in Predisease and in Early Stage Autoimmune Disease MRL/Ipr Mice"; Brain Behavior and Immunity; 2001; pp. 1-16.

Omnitech Electronics, Inc., Olympus 1 Meter × 1 Meter Animal Activity Monitor, 1988.

Omnitech Electronics, Inc., Residential Maze Computerized System, 1991.

Ozer, I. Burak et al.; "A Graph Based Object Description for Information Retrieval in Digital Image and Video Libraries"; Proceedings of IEEE Workshop on Content-Based Access of Image & Video Libraries, Colorado; Jun. 1999; (5pgs).

Ozer, I. Burak et al.; "Human Activity Detection in MPEG Sequence"; Proceedings of IEEE Workshop on Human Motion,, Austin; Dec. 2000; pp. 61-66.

Ozer, I. Burak et al., "Human Detection in Compressed Domain." Proceedings of International Conference on Image Processing, Thessaloniki, Greece, Oct. 2001.

Ozer, I. Burak et al.; "Relational Graph Matching for Human Detection and Posture Recognition"; SPIE, Photonic East 2000, Internet Multimedia Management Systems, Boston; Nov. 2000; (12pgs).

Ozer, W. Wolf et al., "Video Analysis for Smart Rooms," Proc. SPIE vol. 4519, p. 84-90, Internet Multimedia Management Systems II, Jul. 2001.

Palmer, James D. et al., "Approaches to Domain Model Construction", Domain Modeling Workshop, 13.sup.th International Conference on Software Engineering, Austin, Texas; Mar. 26, 1991; pp. 130-135.

Palmer, James D. et al.; "Classification as an Approach to Requirements Analysis"; 1.sup.st ASIS SIG/CR Classification Research Workshop, Toronto, Canada; Nov. 4, 1990; pp. 129-136.

Philips, Michael et al.; "A Multi-Attribute Shot Segmentation Algorithm for Video Programs"; Proceedings, SPIE 2916; 1996; (10pgs).

Philips, Michael et al.; "Video Segmentation Techniques for News"; SPIE, vol. 2916; 1996; pp. 243-251.

RotoScan, Rotometer High Resolution Rotation Monitoring; AccuScan Instruments, Inc., 1993.

Sago, Haruhiko et al.; "Genetic Dissection of Region Associated With Behavioral Abnormalities in Mouse Models for Down Syndrome"; Pediatric Research; vol. 48; No. 5; 2000; pp. 606-613.

Sakic, Boris et al.; "Reduced Corticotropin-Releasing Factor and Enhanced Vasopressin Gene Expression in Brains of Mice With Autoimmunity-Induced Behavioral Dysfunction"; Journal of Neuroimmunology 96; 1999; pp. 80-91.

San Diego Instruments Behavioral Testing Systems, Nov. 19, 1997 (18 pages).

Schrott, Lisa M. et al., "Sensitivity to Foot Shock in Autoimmune NZB .times. NZW F1 Hybrid Mice"; Physiology & Behavior; vol. 56; No. 5; 1994; pp. 849-853.

Schrott, Lisa M. et al.; "Anxiety Behavior, Exploratory Behavior, and Activity in NZB .times. NZW F1 Hybrid Mice: Role of Genotype and Autoimmune Disease Progression"; Brain, Behavior and Immunity; vol. 10; 1996; pp. 260-274.

Schrott, Lisa M. et al.; "Increased Anxiety Behaviors in Autoimmune Mice"; Behavioral Neuoscience; vol. 110; No. 3; 1996; pp. 492-502.

Schrott, Lisa M. et al.; "The Role of Performance Factors in the Active Avoidance-Conditioning Deficit in Autoimmune Mice"; Behavioral Neuroscience; vol. 110; No. 3; 1996; pp. 486-491.

Schrott,, Lisa M. et al.; "Attenuation of Behavioral Abnormalities in Autoimmune Mice by Chronic Soluble Interferon-.gamma. Receptor Treatment"; Brain, Behavior and Immunity; vol. 12; 1998; pp. 90-106.

Segall, M.A. et al.; "A Test of Conditioned Taste Aversion With Mouse Interferon-.alpha."; Brain, Behavior and Immunity; vol. 4; 1990; pp. 223-231.

Segall, M.A. et al.; "An Animal Model for the Behavioral Effects of Interferon"; Behavioral Neuroscience; vol. 104; No. 4; 1990; pp. 612-618.

The Observer, Professional system for collection, analysis and management of observational data, Noldus Information Technology, 1996.

Tremorscan Monitor Model TS1001; AccuScan Instruments, Inc., 1997.

Wolf, W.; "Key Frame Selection by Motion Analysis"; Proceedings, ICASSP, IEEE Press; 1996; (4pgs).

Wolf, Wayne et al.; "A Digital Video Library for Classroom Use"; International Conference on Digital Library '95, Tsukuba; Aug. 1995; (6pgs).

Wolf, Wayne et al.; "A Digital Video Library on the World Wide Web"; ACM Multimedia '96, Addison-Wesley, Publishing Company; Nov. 1996; pp. 433-434.

Wolf, Wayne et al., "A Smart Camera for Real-Time Human Activity Recognition," 2001 IEEE Workshop on Signal Processing Systems, Antwerp, Belgium, Sep. 2001.

Wolf, Wayne; "Hidden Markov Model Parsing of Video Programs"; IEEE; 1997; pp. 2609-2611.

Yeo, B.L. et al.; "Theft-Resistant Video Browsing Using Filtered Versions of Compressed Sequences"; IEEE Conference on Multimedia Computing and Systems; 1995; (6pgs).

Yeung, Minerva M. et al.; "Video Browsing Using Clustering and Scene Transitions on Compressed Sequences"; SPIE Conference on Multimedia Computing and Networking; vol. 2417, 1995; pp. 399-413.

Yu, H. et al.; "A Visual Search System for Video and Image Databases"; IEEE Multimedia; 1997; (8pgs).

Yu, H. et al.; "Hierarchical, Multi-Resolution Algorithms for Dictionary-Driven Content-Based Image Retrieval"; International Conference on Image Processing; 1997; (4pgs).

Yu, H. et al.; "Scenic Classification Methods for Image and Video Databases"; SPIE; vol. 2606; 1995; pp. 363-371.

Yu, Hong-Heather et al.; "A Hierarchical Multiresolution Video Shot Transition Detection Scheme"; Computer Vision and Image Understanding; vol. 75; Jul./Aug. 1999; pp. 196-213.

Yu, Hong-Heather et al.; "Multi-Resolution Video Segmentation Using Wavelet Transformation"; in Storage and Retrieval for Image and Video Databases VI, SPIE; vol. 3312; 1998; pp. 176-187.

Yu, Hong-Heather et al; "A Multi-Resolution Video Segmentation Scheme for Wipe Transition Identification"; in Proceedings IEEE ICASSP; vol. 5; 1998; pp. 2965-2968.

Yu, Hong-Heather et al; "A Visual Search System for Video and Image Databases"; in Proceedings, ICMCS 1997, IEEE Computer Society Press; 1997; pp. 517-524.

Zheng, H. et al; "Data Mining for Combat Vehicle Classification Using Machine Learning"; Applied Imagery and Pattern Recognition (AIPR) '98, Washington, D.C; Oct. 1998; (10pgs).

1

UNIFIED SYSTEM AND METHOD FOR ANIMAL BEHAVIOR CHARACTERIZATION FROM TOP VIEW USING VIDEO ANALYSIS

This application is a continuation of U.S. patent application Ser. No. 10/698,008, filed Oct. 30, 2003, which is a continuation-in-part of U.S. patent application Ser. No. 09/718,374, now U.S. Pat. No. 6,678,413. The subject matter of the related applications is hereby incorporated by reference in its entirety.

GOVERNMENT RIGHTS NOTICE

Portions of the material in this specification arose as a result of Government support under grants MH58964 and MH58964-02 between Clever Sys., Inc. and The National Institute of Mental Health, National Institute of Health. The Government has certain rights in this invention.

BACKGROUND OF THE INVENTION

1. Technical Field

The invention relates generally to behavior analysis of animal objects. More particularly, one aspect of the invention is directed to monitoring and characterization of behaviors under specific behavioral paradigm experiments, including home cage behavior paradigms, locomotion or open field paradigm experiment, object recognition paradigm experiments, variety of maze paradigm experiments, water maze paradigm experiments, freezing paradigm experiments for conditioned fear, for an animal, for example, a mouse or a rat, using video analysis from a top view image or side view image, or the integration of both views.

2. Background Art

Animals, for example mice or rats, are used extensively as human models in the research of drug development; genetic functions; toxicology research; understanding and treatment of diseases; and other research applications. Despite the differing lifestyles of humans and animals, for example mice, their extensive genetic and neuroanatomical homologies give rise to a wide variety of behavioral processes that are widely conserved between species. Exploration of these shared brain functions will shed light on fundamental elements of human behavioral regulation. Therefore, many behavioral test experiments have been designed on animals like mice and rats to explore their behaviors. These experiments include, but not limited to, home cage behaviors, open field locomotion experiments, object recognition experiments, a variety of maze experiments, water maze experiments, and freezing experiments for conditioned fear.

Animal's home cage activity patterns are important examination item on the general health list of animals, such as mice and rats. It provides many important indications of whether the animal's health status is normal or abnormal. Home cage behaviors are best observed by videotaping several 24-hour periods in the animal housing facility, and subsequent scoring of the videotape by two independent observers. However, this observation has rarely been done until our inventions came into play, due to the instability in long term human observation, the time consumed, and the huge costs associated with the observation.

A conventional method for measuring animal's spatial navigation learning and memory is the water maze task, in which the animal swims to find a hidden platform, using visual cues to locate the platform. This task is based on the principle that rodents are highly motivated to escape from a water environment by the quickest, most direct route. (Wenk, 1997) Experiment sessions are usually videotaped, and human observation of videotapes or automated software is used, depending on the parameters required for observing the session.

Variations of popular methods for measuring animal's spatial navigation learning and memory include other maze designs, such as T-maze, Y-maze, and radial arm maze. In all cases, the task requires the animal to choose specific arm(s) of the maze to receive a food or water reinforcement or to avoid a footshock. The shapes of the arms make the differences among T-maze, Y-maze, and radial arm maze. The animal is habituated and then shaped to obtain the reinforcer. Variations of popular methods for measuring animal's anxiety-related behaviors include elevated plus maze, zero maze, etc. Measuring anxiety using elevated plus maze or zero maze rests on the naturalistic conflict between the tendency of animal such as mice to explore a novel environment and the aversive properties of a brightly lit, open area. Elevated plus maze is elevated from the ground about a meter with four (4) arms, two well lit and two closed and dark. Animals such as mice or rats prefer the closed arms but will venture out into the open arms, with a start box in the center. The zero maze is similar, but has annulus of an elevated circular runway, with areas brightly lit alternate with dark, covered areas. We group all of these experiments under "maze". Though the theory and operations and training may be different among these mazes, the observation and measurement is basically similar, i.e., the measurement of animal staying in each arm or arena, closed or open. Experiment session is usually videotaped, and human observation of videotapes or automates software is used, depending on the parameters required for observing the session.

Another method to measure animal's such as mice or rats, capability in spatial learning and memory and their tendency of exploration is the experiment of object recognition, or novelty seeking. Its objective is to measure reduced time spent exploring a novel object that replaced a training object after a specified retention time. Objects of different shapes and colors are placed in an open field, and animal is place in the field. The number of times the animal sniffs at each object, and the duration of each sniffing are measured to show the animal's tendency to explore. Objects are replaced with new objects from time to time. The experiment session is videotaped, and human observation of videotapes is used to measure those parameters.

The most standardized general measure of motor function is spontaneous activity in the open field. Square, rectangular, and circular equipment is presently in common use. Sizes of open fields range from centimeters to several meters. Scoring of videotaped session allows quantization of animal's spontaneous activity. Automated open fields now routinely used in behavioral neuroscience laboratories are equipped with either photocell beams or video tracking and computer software. Both types of automated systems calculate a useful range of basic locomotor parameters.

Freezing test is designed for cued and contextual fear conditioning, which is among the most intuitive memory paradigms. Freezing is a common response feared situation in many species, and is defined as no movements other than respiration. Conditioning training consists of placing the mouse in the chamber and exposing to a mild footshock paired with auditory cue. Freezing is measured when the trained mouse is placed back in the same chamber for training with auditory cue, and scored for bouts of freezing behavior. Human observation of videotapes of the session is used for this scoring, which is inaccurate and expensive. Automated system using mechanical principle exists to help real-time scoring of freezing. However, the precision of such a mechanical system need to be further improved.

As discussed, all these apparatus and experiments use, in many cases, human observation of videotapes of the experiment sessions, resulting in inaccuracy, subjectivity, labor-intensive, and thus expensive experiments. Some automating software provides rudimentary and basic parameters, relying on tracking animal as a point in space, generating experiment results that are inaccurate and can not meet the demands for advanced features. Besides, each system software module works for only a specific experiment, resulting in potential discrepancy in the results across different systems due to differences in software algorithms used.

All the observations of these behavioral experiments use video to record experiment processes and rely human observations. This introduces the opportunity to utilize the latest technologies development in computer vision, image processing, and digital video processing to automate the processes and achieve better results, high throughput screening, and lower costs. Many of these experiments are conducted with observations performed from top view, that is, observation of the experiments from above the apparatus is used to obtain needed parameters. This also provides an opportunity to unify the approaches to observe and analyze these experiments' results.

SUMMARY OF THE INVENTION

There are strong needs for automated systems and software that can automate the measurements of the experiments mentioned above, provide the measurements of meaningful complex behaviors and revealing new parameters that characterize animal behaviors to meet post-genomic era's demands, and obtain consistent results using novel approaches.

A revolutionary approach is invented to automatically measure animal's home cage activity patterns. This approach consists of defining a unique set of animal's, such as mice or rats, behavior category. This category includes behaviors like rearing, walking, grooming, eating, drinking, jumping, hanging, etc. Computer systems are designed and implemented that can produce digital video files of animal's behaviors in a home cage in real time or off-line mode. Software algorithms are developed to automatically understand the animal's behaviors in those video files.

A novel and unified framework is provided for automatically analyzing animal behaviors from multiple different behavioral paradigms. This unified framework lays the foundation and constitutes the common layer for all the automated measurements in the experiments of water maze, maze, locomotion, object recognition, and freezing for fear conditioning.

Creative algorithms are designed to support innovative analysis of behaviors of animals such as mice or rats. This analysis is based on the premise that the entire animal body, body parts, related color information, and their dynamic motion are taken advantage of in order to provide the measurement of complex behaviors and novel parameters.

Virtual apparatus is designed and implemented in the system to ensure same software framework can be applied to different apparatuses such as water maze, variations of mazes including T-maze, Y-maze, radial arm maze, elevated plus maze, zero maze, cages of rectangular, circular, or any other shapes, and object of any color and shapes, instead of having different software component to handle different apparatus. The software is designed to provide graphic tools, and users can use these graphic tools to create virtual apparatus corresponding to the real apparatus that is being used for the experiment under observation. Graphic tools also provide the capability to calibrate these apparatus, allowing better identification of behaviors and precise measurement of behaviors in real measurements instead of relative measurement using number of pixels.

Virtual zones are another invention that has been implemented in the system. In all the experiments, the animal is moving around the cage, and the activity distribution in different zones of the cage is of great interest to many scientists. The conventional approach is to use infrared photobeams to divide the cage into zones Photobeams are released from tubes at one end, and a sensor on the opposite end receives the photobeams. When photobeams are interrupted by the animal, the receiver records the signal. In this way, the animal can move around while their activity distribution across zones is recorded and calculated. In this invention, virtual zones are used instead of the zones created by photobeams. Graphic tools are designed and provided for the users. Users draw the zones as they want using the graphic tools. The software tracks the animals and records how the animal crosses the zones and stay in the zones as defined by the user.

Another invention is that algorithms are designed and implemented to allow different modules to be combined to achieve multiple experiment purposes in a joint operation. For one example, measuring animal's object recognition behaviors and measuring animal's locomotion activity can be performed during one experiment operation. The users can perform their regular object recognition experiment. However, software modules of object recognition and locomotion analysis are both executed to obtain analysis results of both. This flexibility enhances the power and usability of the system.

In general, the present invention is directed to systems and methods for finding patterns of behaviors and/or activities of an animal using video. The invention includes a system with a video camera connected to a computer in which the computer is configured to automatically provide animal identification, animal motion tracking (for moving animal), animal shape, animal body parts, and posture classification, and behavior identification. Thus, the present invention is capable of automatically monitoring a video image to identify, track and classify the actions of various animals and their movements. The video image may be provided in real time from a camera and/or from a storage location. The invention is particularly useful for monitoring and classifying mice or rats behavior for testing drugs and genetic mutations, but may be used in any of a number of surveillance or other applications.

In one embodiment the invention includes a system in which an analog/digital video camera and a video record/playback device (e.g., VCR) are coupled to a video digitization/compression unit. The video camera may provide a video image containing an animal to be identified. The video digitization/compression unit is coupled to a computer that is configured to automatically monitor the video image to identify, track and classify the actions of the animal and its movements over time within a sequence of video session image frames. The digitization/compression unit may convert analog video and audio into, for example, MPEG or other formats. The computer may be, for example, a personal computer, using either a Windows platform or a Unix platform, or a MacIntosh computer and compatible platform. The computer is loaded and configured with custom software programs (or equipped with firmware) using, for example, MATLAB or C/C++ programming language, so as to analyze the digitized video for animal identification and segmentation, tracking, and/or behavior/activity characterization. This software may be stored in, for example, a program memory, which may include ROM, RAM, CD ROM and/or a hard drive, etc. In one variation of the invention the software (or firmware) includes a unique background subtraction method which is more simple, efficient, and accurate than those previously known.

In operation, the system receives incoming video images from either the video camera in real time or pre-recorded from the video record/playback unit. If the video is in analog format, then the information is converted from analog to digital format and may be compressed by the video digitization/compression unit. The digital video images are then provided to the computer where various processes are undertaken to identify and segment a predetermined animal from the image. In a preferred embodiment the animal is a mouse or rat in motion with some movement from frame to frame in the video, and is in the foreground of the video images. In any case, the digital images may be processed to identify and segregate a desired (predetermined) animal from the various frames of incoming video. This process may be achieved using, for example, background subtraction, mixture modeling, robust estimation, and/or other processes.

The shape and location of the desired animal is then tracked from one frame or scene to another frame or scene of video images. The body parts of the animal such as head, mouth, and tail are identified by novel approaches through body contour segmentation, contour segment classification, and relaxation labeling. Next, the changes in the shapes, locations, body parts, and/or postures of the animal of interest may be identified, their features extracted. Then, the shape, location, body parts, and other related information may be used to characterize the animal's activity into one of a number of pre-defined behaviors. For example, if the animal is a mouse or rat, some pre-defined normal behaviors may include sleeping, walking, sniffing, etc., and pre-defined abnormal behavior may include spinning vertical, jumping in the same spot, etc. The pre-defined behaviors may be stored in a database in the data memory. The behavior may be characterized using, for example, approaches such as rule-based analysis, token parsing procedure, and/or Hidden Markov Modeling (HMM). Further, the system may be constructed to characterize the object behavior as new behavior and particular temporal rhythm.

In another preferred embodiment directed towards the video camera providing a video image containing animals such as mice or rats to be identified, the system operates as follows. There is at least one camera, or multiple cameras, taking video image of experiment apparatus that contain animals. There is at least one apparatus, or as many as the computer computing power allows, say four (4) or sixteen (16) or even more. Each apparatus contains at least one animal or multiple animals. The multiple cameras may be taking video from different points of views such as one taking video images from the side of the apparatus, or one taking video images from the top of the apparatus. These apparatus can be home cage, open field cage, water maze device, T-maze device, Y-maze device, radial arm device, zero maze device, elevated plus maze device, or other experiment devices. When video images are taken of multiple apparatuses and devices containing one or multiple animals, and are analyzed for identifying these animals' behaviors, high throughput screening is achieved. When video images taken from different points of views, for example, one from the top view and another from the side view, are combined to identify animal's behaviors, integrated analysis is achieved.

In another preferred embodiment directed toward video analysis of animals such as mice or rats, the system operates as follows. As a preliminary matter, normal postures and behaviors of the animals are defined and may be entered into a Normal Paradigm Parameters, Postures and Behaviors database. In analyzing, in a first instant, incoming video images are received. The system determines if the video images are in analog or digital format and input into a computer. If the video images are in analog format they are digitized and may be compressed, using, for example, an MPEG digitizer/compression unit. Otherwise, the digital video image may be input directly to the computer. Next, a background may be generated or updated from the digital video images and foreground objects detected. Next, the foreground animal features are extracted. Also, body parts such as head, tail, ear, mouth, forelimbs, hind limbs, abdomen, and upper and lower back, are identified. Two different methods are pursuing from this point, depending on different behavior paradigms. In one method, the foreground animal shape is classified into various categories, for example, standing, sitting, etc. Next, the foreground animal posture is compared to the various predefined postures stored in the database, and then identified as a particular posture or a new (unidentified) posture. Then, various groups of postures and body parts are concatenated into a series to make up a foreground animal behavior compared against the sequence of postures, stored in for example a database in memory, that make up known normal or abnormal behaviors of the animal. The abnormal behaviors are then identified in terms of known abnormal behavior, new behavior and/or daily rhythm. In another method, behavioral processes and events are detected, and behavior parameters are calculated. These behaviors parameters give indications to animal health information related to learning and memory capability, anxiety, and relations to certain diseases.

In one variation of the invention, animal detection is performed through a unique method of background subtraction. First, the incoming digital video signal is split into individual images (frames) in real-time. Then, the system determines if the background image derived from prior incoming video needs to be updated due to changes in the background image or a background image needs to be developed because there was no background image was previously developed. If the background image needs to be generated, then a number of frames of video image, for example 20, will be grouped into a sample of images. Then, the system creates a standard deviation map of the sample of images. Next, the process removes a bounding box area in each frame or image where the variation within the group of images is above a predetermined threshold (i.e., where the object of interest or moving objects are located). Then, the various images within the sample less the bounding box area are averaged. Final background is obtained by averaging 5-10 samples. This completes the background generation process. However, often the background image does not remain constant for a great length of time due to various reasons. Thus, the background needs to be dynamically recalculated periodically as above or it can be recalculated by keeping track of the difference image and note any sudden changes. The newly dynamically generated background image is next subtracted from the current video image(s) to obtain foreground areas that may include the object of interest.

Next, the object identification/detection process is performed. First, regions of interest (ROI) are obtained by identifying areas where the intensity difference generated from the subtraction is greater than a predetermined threshold, which constitute potential foreground object(s) being sought. Classification of these foreground regions of interest will be performed using the sizes of the ROIs, distances among these ROIs, threshold of intensity, and connectedness, to thereby identify the foreground objects. Next, the foreground object identification/detection process may be refined by adaptively learning histograms of foreground ROIs and using edge detection to more accurately identify the desired object(s). Finally, the information identifying the desired foreground object is output. The process may then continue with the tracking and/or behavior characterization step(s).

The previous embodiments are particularly applicable to the study and analysis of mice or rats used in genetic and drug experimentation. Another variation of the present invention is directed to automatically determining locomotion behavior of mice or rats in an open field. Once the animal is identified as foreground object as discussed above, the body parts of the animal such as head and tail, and hind limbs and forelimbs, and center of mass, are identified. The traces of the path of the movements of the animal's center of mass in the open field under observation is recorded, its instant and average speed of movements and distance traveled are calculated, its instant and cumulative body turning angles are analyzed. In addition, events like turning ratio (ratio of path length over number of turns, where number of turns is counted when the animal makes a turn larger than 80 degrees when the animal travels one body length); proximity score (calculated by determining the distance of the animal from the goal during each second of the trial and is used as a measure of deviation from the ideal path to the platform once an animal is placed in the cage); heading errors (defined as an instance of swimming away from the VISIBLE platform); and animal staying in a specific zone inside the field, are recorded. Then a visualization process will further analyze the result of the path trace recorded to generate variety of statistic results. Visualization process allows users to use graphic drawing tools to define any number of zones of any shape in the open field as needed. The system provides a graphic tool that allows users to define the field of any shape.

The previous embodiments are particularly applicable to the study and analysis of mice or rats in their capability to explore new objects. Another variation of the present invention is directed to automatically determining the object recognition activity. Graphic tools are provided to allow users to define objects in the scene. Once the animal is identified as a foreground object as discussed above, the body parts of the animal such as head and tail and hind limbs and forelimbs, and center of mass are identified. The traces of the path of the movements of the animal's center of mass are recorded. The distances of the animal's head to any of the objects in the scene are calculated and when the distance to an object is less than a user-defined amount, the animal is counted as animal's sniffing at the object and is said to be exploring that object. Statistics about these exploring events are generated and exported.

The previous embodiments are particularly applicable to the study and analysis of mice or rats in their spatial learning and memory. Third variation of the present invention is directed to automatically determining the behaviors of mice or rats in a water maze experiment environment. Graphic tools are provided to allow users to define the maze and platforms. Once the animal is identified as a foreground object as discussed above, the body parts of the animal such as head and tail and hind limbs and forelimbs, and center of mass are identified. The traces of the path of the movements of the animal's center of mass are recorded. The latency (the time period the animal spent in swimming in the water before landing at the platform) is measured; its instant and average speed of movements and distance traveled are calculated; its instant and cumulative body turning angles are analyzed. In addition, events like turning ratio (ratio of path length over number of turns, where number of turns is counted when the animal makes a turn larger than 90 degrees when the animal travels one body length); proximity score (calculated by determining the distance of the animal from the goal (platform) during each second of the trial and is used as a measure of deviation from the ideal path to the platform once an animal is placed in the water); heading errors (defined as an instance of swimming away from the VISIBLE platform); and animal staying in a specific zone inside the maze, are recorded. Then a visualization process will further analyze the result of the path trace recorded to generate variety of statistic results. Visualization process allows users to use graphic drawing tools to define any number of zones of any shape in the open field as needed. The system provides a graphic tool that allows users to define the field of any shape.

The previous embodiments are particularly applicable to the study and analysis of mice or rats in their spatial learning and memory and anxiety. Fourth variation of the present invention is directed to automatically determining the behaviors of mice or rats in a variety of maze apparatus. Graphic tools are provided to define specific maze apparatus, such as T-maze, Y-maze, radial arm maze, zero maze, elevated plus maze, and etc. Once the animal is identified as a foreground object as discussed above, the body parts of the animal such as head and tail and hind limbs and forelimbs, and center of mass are identified. The traces of the path of the movements of the animal's center of mass are recorded. More importantly, the animal's behaviors related to every arm in the maze, such as time spent in each arm, the number of times entering and exiting an arm, are found. Besides, animal's instant and average speed of movements and distance traveled are calculated; its instant and cumulative body turning angles are analyzed. In addition, events such as animal partial incursions into particular arm (for example, the animal might maintain its hind quarters in a closed arm while poking its nose into an open arm); Stretch-Attend Behavior; Head-Dipping behavior; and Supported Rearing, are detected.

Fifth variation of the present invention is directed to automatically determining the freezing behaviors of mice or rats in a cued or conditioned fear tests. Graphic tools are provided. Graphic tools are provided to define the area within which animal activity is measured. Differences between neighboring frames are compared pixel-by-pixel in terms of their intensity and color intensity. These differences are used to calculate the motion of the animal from frame-to-frame because motion in the area is caused by movements of the animal. The values of these differences indicate if the animal is moving or freezing.

Development activities have been completed to validate various scientific definitions of mouse behaviors and to create novel digital video processing algorithms for mouse tracking and behavior recognition, which are embodied in a software and hardware system according to the present invention. An automated method for analysis of mouse behavior from digitized 24 hours video has been achieved using the present invention and its digital video analysis method for object identification and segmentation, tracking, and classification. Several different methods and their algorithms, including Background Subtraction, Probabilistic approach with Expectation-Maximization, and Robust Estimation to find parameter values by best fitting a set of data measurements and results proved successful.

The previous embodiments are particularly applicable to the study and analysis of mice or rats used in genetic and drug experimentation. One variation of the present invention is directed particularly to automatically determining the behavioral characteristics of a mouse in a home cage, a cage looking like a shoebox used for housing animals. The need for sensitive detection of novel phenotypes of genetically manipulated or drug-administered mice demands automation of analyses. Behavioral phenotypes are often best detected when mice are unconstrained by experimenter manipulation. Thus, automation of analysis of behavior in a known environment, for example a home cage, would be a powerful tool for detecting phenotypes resulting from gene manipulations or drug administrations. Automation of analysis would allow quantification of all behaviors as they vary across the daily cycle of activity. Because gene defects causing developmental disorders in humans usually result in changes in the daily rhythm of behavior, analysis of organized patterns of behavior across the day may also be effective in detecting phenotypes in transgenic and targeted mutant mice. The automated system may also be able to detect behaviors that do not normally occur and present the investigator with video clips of such behavior without the investigator having to view an entire day or long period of mouse activity to manually identify the desired behavior.

The systematically developed definition of mouse behavior that is detectable by the automated analysis according to the present invention makes precise and quantitative analysis of the entire mouse behavior repertoire possible for the first time. The various computer algorithms included in the invention for automating behavior analysis based on the behavior definitions ensure accurate and efficient identification of mouse behaviors. In addition, the digital video analysis techniques of the present invention improves analysis of behavior by leading to: (1) decreased variance due to non-disturbed observation of the animal; (2) increased experiment sensitivity due to the greater number of behaviors sampled over a much longer time span than ever before possible; and (3) the potential to be applied to all common normative behavior patterns, capability to assess subtle behavioral states, and detection of changes of behavior patterns in addition to individual behaviors.

The invention may identify some abnormal behavior by using video image information (for example, stored in memory) of known abnormal animals to build a video profile for that behavior. For example, video image of vertical spinning while hanging from the cage top was stored to memory and used to automatically identify such activity in mice. Further, abnormalities may also result from an increase in any particular type of normal behavior. Detection of such new abnormal behaviors may be achieved by the present invention detecting, for example, segments of behavior that do not fit the standard profile. The standard profile may be developed for a particular strain of mouse whereas detection of abnormal amounts of a normal behavior can be detected by comparison to the statistical properties of the standard profile.

Thus, the automated analysis of the present invention may be used to build profiles of the behaviors, their amount, duration, and daily cycle for each animal, for example each commonly used strain of mice. A plurality of such profiles may be stored in, for example, a database in a data memory of the computer. One or more of these profiles may then be compared to a mouse in question and difference from the profile expressed quantitatively.

The techniques developed with the present invention for automation of the categorization and quantification of all home-cage mouse behaviors throughout the daily cycle is a powerful tool for detecting phenotypic effects of gene manipulations in mice. As previously discussed, this technology is extendable to other behavior studies of animals and humans, as well as surveillance purposes. As will be described in detail below, the present invention provides automated systems and methods for automated accurate identification, tracking and behavior categorization of an object whose image is captured with video.

Other variations of the present invention is directed particularly to automatically determining the behavioral characteristics of an animal in various behavioral experiment apparatus such as water maze, Y-maze, T-maze, zero maze, elevated plus maze, locomotion open field, field for object recognition study, and cued or conditioned fear. In these experiment apparatuses, animal's body contour, center of mass, body parts including head, tail, forelimbs, hind limbs and etc. are accurately identified using the embodiments above. This allows excellent understanding of animal's behaviors within these specific experiment apparatus and procedures. Many novel and important parameters, which were beyond reach previously, are now successfully analyzed. These parameters include, but not limited to, traces of path of animal's center of mass, instant and average speed, instant and average of body turning angles, distance traveled, turning ratio, proximity score, heading error, stretch-and-attend, head-dipping, stay-across-arms, supported-rearing, sniffing (exploring) at particular objects, latency time to get to the goal (platform), time spent in specific arm/arena or specific zones within arm/arena, number of time entering and exiting arm/arena or specific zones within arm/arena, and etc. These parameters provide good indications for gene targeting, drug screening, toxicology research, learning and memory process study, anxiety study, understanding and treatment of diseases such as Parkinson's Disease, Alzheimer Disease, ALS, and etc.

DESCRIPTION OF THE PREFERRED EMBODIMENTS

Figure 1:
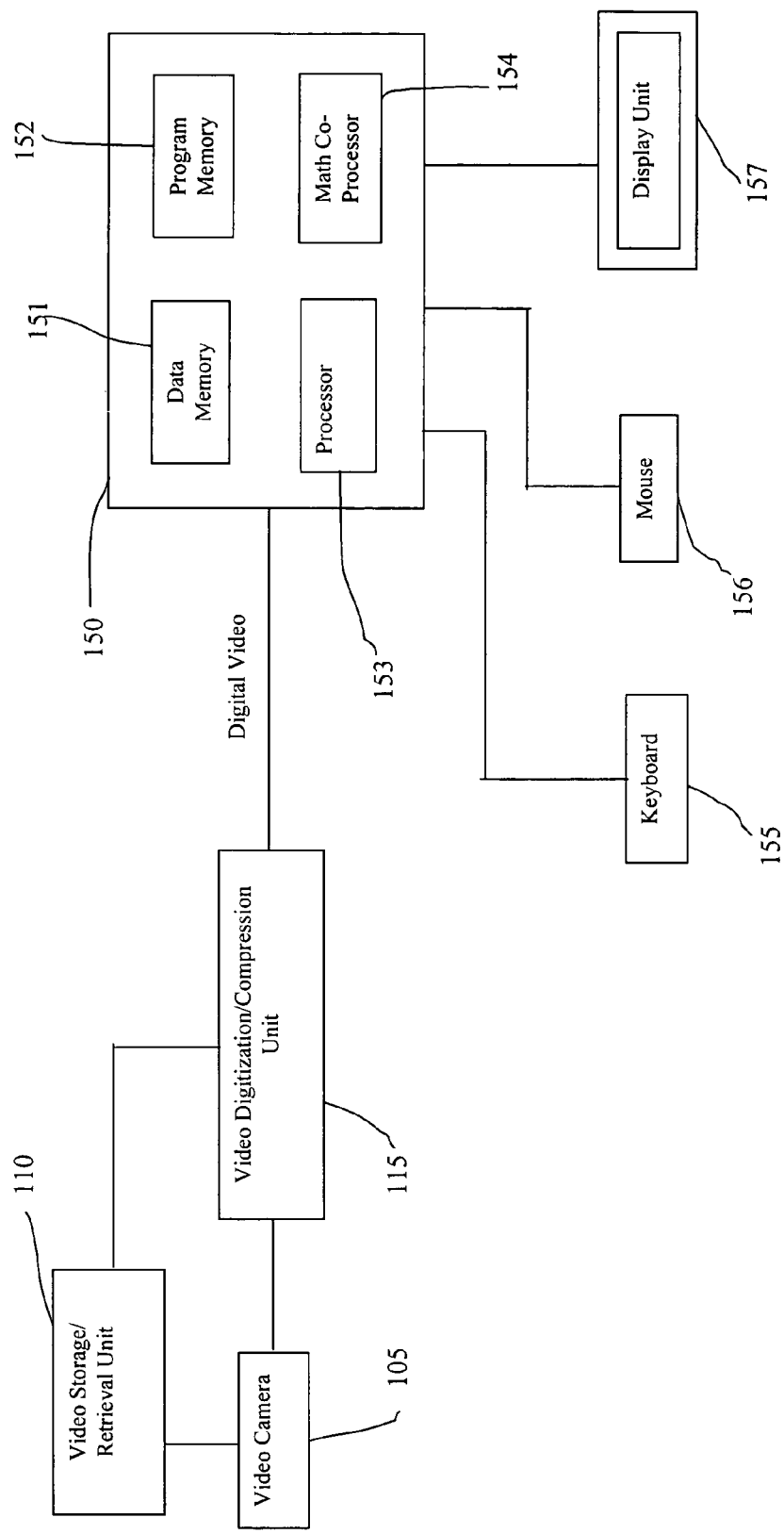
FIG. 1 is a block diagram of one exemplary system configurable to find the position, shape, and behavioral characteristics of an object using automated video analysis, according to one embodiment of the present invention.

The past few years have seen an increase in the integration of video camera and computer technologies. Today, the integration of the two technologies allows video images to be digitized, stored, and viewed on small inexpensive computers, for example, a personal computer. Further, the processing and storage capabilities of these small inexpensive computers has expanded rapidly and reduced the cost for performing data and computational intensive applications. Thus, video analysis systems may now be configured to provide robust surveillance systems that can provide automated analysis and identification of various objects and characterization of their behavior. The present invention provides such systems and related methods.

In general, the present invention can automatically find the patterns of behaviors and/or activities of a predetermined object being monitored using video. The invention includes a system with a video camera connected to a computer in which the computer is configured to automatically provide object identification, object motion tracking (for moving objects), object shape classification, and behavior identification. In a preferred embodiment the system includes various video analysis algorithms. The computer processes analyze digitized video with the various algorithms so as to automatically monitor a video image to identify, track and classify the actions of one or more predetermined objects and its movements captured by the video image as it occurs from one video frame or scene to another. The system may characterize behavior by accessing a database of object information of known behavior of the predetermined object. The image to be analyzed may be provided in real time from one or more camera and/or from storage.

In various exemplary embodiments described in detail as follows, the invention is configured to enable monitoring and classifying of animal behavior that result from testing drugs and genetic mutations on animals. However, as indicated above, the system may be similarly configured for use in any of a number of surveillance or other applications. For example, the invention can be applied to various situations in which tracking moving objects is needed. One such situation is security surveillance in public areas like airports, military bases, or home security systems. The system may be useful in automatically identifying and notifying proper law enforcement officials if a crime is being committed and/or a particular behavior being monitored is identified. The system may be useful for monitoring of parking security or moving traffic at intersections so as to automatically identify and track vehicle activity. The system may be configured to automatically determine if a vehicle is speeding or has performed some other traffic violation. Further, the system may be configured to automatically identify and characterize human behavior involving guns or human activity related to robberies or thefts. Similarly, the invention may be capable of identifying and understanding subtle behaviors involving portions of body such as forelimb and can be applied to identify and understand human gesture recognition. This could help deaf individuals communicate. The invention may also be the basis for computer understanding of human gesture to enhance the present human-computer interface experience, where gestures will be used to interface with computers. The economic potential of applications in computer-human interface applications and in surveillance and monitoring applications is enormous.

In one preferred embodiment illustrated in FIG. 1, the invention includes a system in which an analog video camera 105 and a video storage/retrieval unit 110 may be coupled to each other and to a video digitization/compression unit 115. The video camera 105 may provide a real time video image containing an object to be identified. The video storage/retrieval unit 110 may be, for example, a VCR, DVD, CD or hard disk unit. The video digitization/compression unit 115 is coupled to a computer 150 that is configured to automatically monitor a video image to identify, track and classify the actions (or state) of the object and its movements (or stillness) over time within a sequence of images. The digitization/compression unit 115 may convert analog video and audio into, for example, MPEG format, Real Player format, etc. The computer may be, for example, a personal computer, using either a Windows platform or a Unix platform, or a Macintosh computer and compatible platform. In one variation the computer may include a number of components such as (1) a data memory 151, for example, a hard drive or other type of volatile or non-volatile memory; (2) a program memory 152, for example, RAM, ROM, EEPROM, etc. that may be volatile or non-volatile memory; (3) a processor 153, for example, a microprocessor; and (4) a second processor to manage the computation intensive features of the system, for example, a math coprocessor 154. The computer may also include a video processor such as an MPEG encoder/decoder. Although the computer 150 has been shown in FIG. 1 to include two memories (data memory 151 and program memory 152) and two processors (processor 153 and math co-processor 154), in one variation the computer may include only a single processor and single memory device or more then two processors and more than two memory devices. Further, the computer 150 may be equipped with user interface components such as a keyboard 155, electronic mouse 156, and display unit 157.

In one variation, the system may be simplified by using all digital components such as a digital video camera and a digital video storage/retrieval unit 110, which may be one integral unit. In this case, the video digitization/compression unit 115 may not be needed.

The computer is loaded and configured with custom software program(s) (or equipped with firmware) using, for example, MATLAB or C/C++ programming language, so as to analyze the digitized video for object identification and segmentation, tracking, and/or behavior/activity characterization. This software may be stored in, for example, a program memory 152 or data memory that may include ROM, RAM, CD ROM and/or a hard drive, etc. In one variation of the invention the software (or firmware) includes a unique background subtraction method which is more simple, efficient, and accurate than those previously known which will be discussed in detail below.

Figure 2:
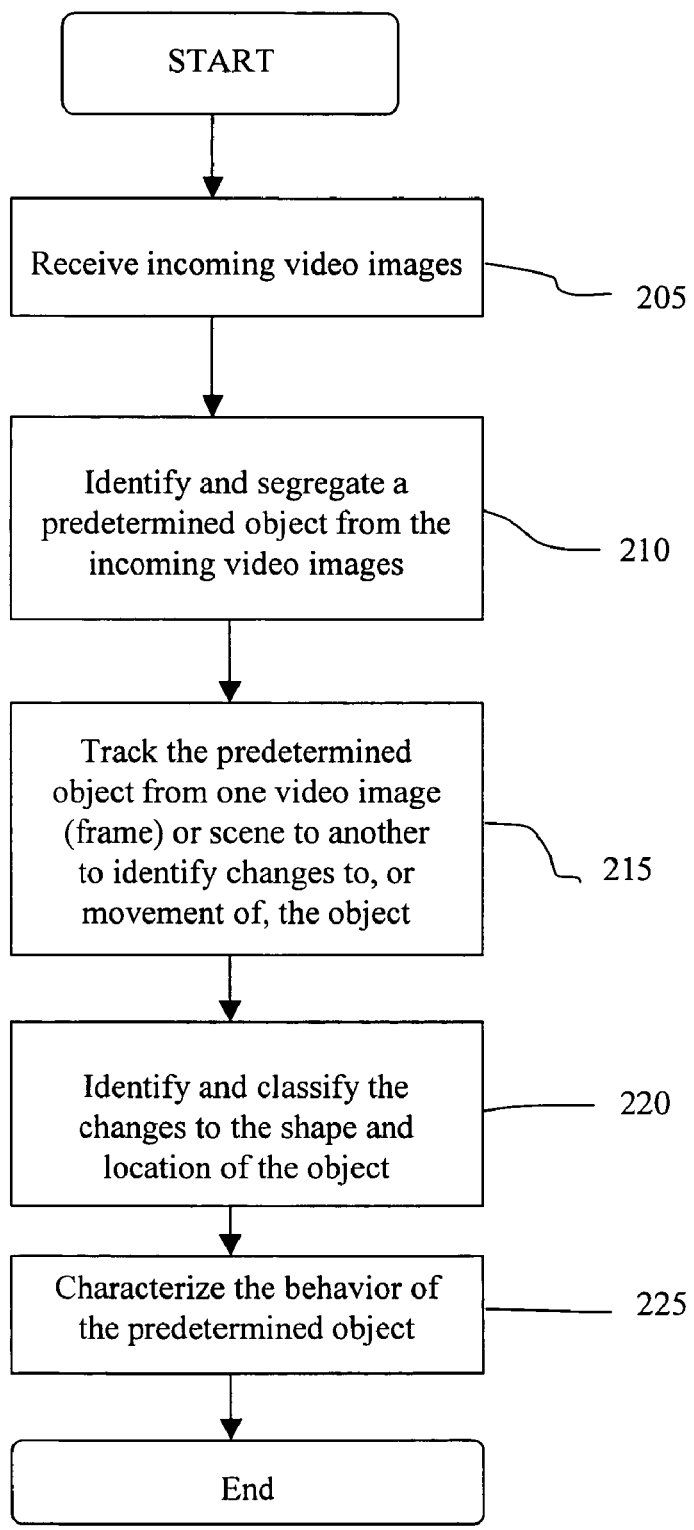
FIG. 2 is a flow chart of a method of automatic video analysis for object identification and characterization, according to one embodiment of the present invention.

Referring to FIG. 2, a general method of operation for one embodiment of the invention will be described. In operation, in the video analysis mode the system may receive incoming video images at step 205, from the video camera 105 in real time, pre-recorded from the video storage/retrieval unit 110, and/or a memory integral to the computer 150. If the video is in analog format, then the information is converted from analog to digital format and may be compressed by the video digitization/compression unit 115. The digital video images are then provided to the computer 150 for various computational intensive processing to identify and segment a predetermined object from the image. In a preferred embodiment, the object to be identified and whose activities are to be characterized is a moving object, for example a mouse, which has some movement from frame to frame or scene to scene in the video images and is generally in the foreground of the video images. In any case, at step 210 the digital images may be processed to identify and segregate a desired (predetermined) object from the various frames of incoming video. This process may be achieved using, for example, background subtraction, mixture modeling, robust estimation, and/or other processes.

Next, at step 215, various movements (or still shapes) of the desired object may then be tracked from one frame or scene to another frame or scene of video images. As will be discussed in more detail below, this tracking may be achieved by, for example, tracking the outline contour of the object from one frame or scene to another as it varies from shape to shape and/or location to location. Next, at step 220, the changes in the motion of the object, such as the shapes and locations of the object of interest may be identified and their features extracted, and the positions of various feature points or segments of the object such as animal head, animal tail, animal hind body etc. may be identified and their features extracted. Then, at step 225, the states of the object, for example the shape, location, and feature points and segments information may be used to characterize the objects activity into one of a number of pre-defined behaviors or events. For example, if the object is an animal, some pre-defined behaviors may include walking, turning, sniffing, etc. The pre-defined behaviors may be stored in a database in the data memory 151.

Types of behavior may also be characterized using, for example, approaches such as rule-based label analysis or token parsing procedure. From these methods, the system may be capable of characterizing the object behavior as new behavior and particular temporal rhythm.

The previous embodiments are generally applicable to identifying, tracking, and characterizing the activities of a particular object of interest present in a video image, e.g., an animal, a human, a vehicle, etc. However, the invention is also particularly applicable to the study and analysis of animals used for testing new drugs and/or genetic mutations. As such, a number of variations of the invention related to determining changes in behavior of mice will be described in more detail below using examples of video images obtained.

One variation of the present invention is designed particularly for the purpose of automatically determining the behavioral characteristics of a mouse. The need for sensitive detection of novel phenotypes of genetically manipulated or drug-administered mice demands automation of analyses. Behavioral phenotypes are often best detected when mice are unconstrained by experimenter manipulation. Thus, automation of analysis of behavior in a home cage would be a preferred means of detecting phenotypes resulting from gene manipulations or drug administrations. Automation of analysis as provided by the present invention will allow quantification of all behaviors and may provide analysis of the mouse's behavior as they vary across the daily cycle of activity. Because gene defects causing developmental disorders in humans usually result in changes in the daily rhythm of behavior, analysis of organized patterns of behavior across the day may be effective in detecting phenotypes in transgenic and targeted mutant mice. The automated system of the present invention may also detect behaviors that do not normally occur and present the investigator with video clips of such behavior without the investigator having to view an entire day or long period of mouse activity to manually identify the desired behavior.

The systematically developed definition of mouse behavior that is detectable by the automated analysis of the present invention makes precise and quantitative analysis of the entire mouse behavior repertoire possible for the first time. The various computer algorithms included in the invention for automating behavior analysis based on the behavior definitions ensure accurate and efficient identification of mouse behaviors. In addition, the digital video analysis techniques of the present invention improves analysis of behavior by leading to: (1) decreased variance due to non-disturbed observation of the animal; (2) increased experiment sensitivity due to the greater number of behaviors sampled over a much longer time span than ever before possible; and (3) the potential to be applied to all common normative behavior patterns, capability to assess subtle behavioral states, and detection of changes of behavior patterns in addition to individual behaviors. Development activities have been complete to validate various scientific definition of mouse behaviors and to create novel digital video processing algorithms for mouse tracking and behavior recognition, which are embody in software and hardware system according to the present invention.

Various lighting options for videotaping have been evaluated. Lighting at night as well as with night vision cameras was evaluated. It has been determined that good quality video was obtained with normal commercial video cameras using dim red light, a frequency that is not visible to rodents. Videos were taken in a standard laboratory environment using commercially available cameras 105, for example a Sony analog camera, to ensure that the computer algorithms developed would be applicable to the quality of video available in the average laboratory. The commercially available cameras with white lighting gave good results during the daytime and dim red lighting gave good results at night time.

Referring again to FIG. 2, the first step in the analysis of mouse behavior is an automated initialization step that involves analysis of video images to identify the location and outline of the mouse, as indicated by step 210. Second, the location and outline of the mouse are tracked over time, as indicated by step 215. Performing the initialization step periodically may be used to reset any propagation errors that appear during the tracking step. As the mouse is tracked over time, its features including shape are extracted, and used for training and classifying the posture and body parts of the mouse from frame to frame, as indicated by step 220. Using this posture and body part information and all related information about the orientation, shape, and position of the mouse generated for each frame, the actual behavior is determined by their relationship over time, as indicated by step 225.

I. Location and Outline Identification and Feature Extraction

The first step in analyzing a video of an animal and to analyze the behavior of the animal is to locate and extract the animal. A pre-generated background of the video clip in question is first obtained and it is used to determine the foreground objects by taking the intensity difference and applying a threshold procedure to remove noise. This step may involve threshold procedures on both the intensity and the size of region. An 8-connection labeling procedure may be performed to screen out disconnected small noisy regions and improve the region that corresponds to the mouse. In the labeling process, all pixels in a frame will be assigned a label as foreground pixel or background pixel based on the threshold. The foreground pixels are further cleaned up by removing smaller components and leaving only the largest component as the foreground object. Those foreground pixels that border a background pixel form the contour for the object. The outline or contour of this foreground object is thus determined. The centroid (or center of mass) of the foreground object is calculated and is used for representing the location of the object (e.g., mouse).

The contour representation can be used as features of the foreground object, in addition to other features that include but not limited to: centroid, the principal orientation angle of the object, the area (number of pixels), the eccentricity (roundness), and the aspect ratio of object.

II. Mouse Tracking

Ideal tracking of foreground objects in the image domain involves a matching operation to be performed that identifies corresponding points from one frame to the next. This process may become computationally too consuming or expensive to perform in an efficient manner. Thus, one approach is to use approximations to the ideal case that can be accomplished in a short amount of time. For example, tracking the foreground object may be achieved by merely tracking the outline contour from one frame to the next in the feature space (i.e., identified foreground object image).

In one variation of the invention, tracking is performed in the feature space, which provides a close approximation to tracking in the image domain. The features include the centroid, principal orientation angle of the object, area (number of pixels), eccentricity (roundness), and the aspect ratio of object with lengths measured along the secondary and primary axes of the object. In this case, let S be the set of pixels in the foreground object, A denote the area in number of pixels, ($C_x$, $C_y$) denote the centroid, $\phi$ denote the orientation angle, E denote the eccentricity, and R denote the aspect ratio. Then, $$C_x = \frac{1}{A}\sum_S x$$

$$C_y = \frac{1}{A}\sum_S y$$

Let us define three intermediate terms, called second order moments, $$m_{2,0} = \sum_S (x - C_x)^2$$

$$m_{0,2} = \sum_S (y - C_y)^2$$

$$m_{1,1} = \sum_S (x - C_x)(y - C_y)$$

Using the central moments, we define, $$\phi = \frac{1}{2}\arctan\frac{2m_{1,1}}{m_{2,0} - m_{0,2}}$$

$$E = \frac{(m_{2,0} - m_{0,2})^2 + 4m_{1,1}^2}{(m_{2,0} - m_{0,2})^2}$$

R is equal to the ratio of the length of the range of the points projected along an axis perpendicular to $\phi$, to the length of the range of the points projected along an axis parallel to $\phi$. This may also be defined as the aspect ratio (ratio of width to length) after rotating the foreground object by $\phi$.

Tracking in the feature space involves following feature values from one frame to the next. For example, if the area steadily increases, it could mean that the mouse is coming out of a cuddled up position to a more elongated position, or that it could be moving from a front view to a side view, etc. If the position of the centroid of the mouse moves up, it means that the mouse may be rearing up on its hind legs. Similarly, if the angle of orientation changes from horizontal to vertical, it may be rearing up. These changes can be analyzed with combinations of features also.

However, it is possible for a contour representation to be used to perform near-optimal tracking efficiently in the image domain (i.e., the complete image before background is subtracted).

III. Mouse Feature Points and Segments Identification

Once the features are obtained for the frames in the video sequence, the foreground state of the mouse is determined by identifying certain important feature points and segments on the mouse such as the head, tail, waist, fore body and hind body.

The head is detected by using a combination of features including direction of motion, distance to tip from the center of mass, the curvature at that point, and the tail information. The head is not on the side of the tail, but, on the other side.

The tail is detected using a combination of shape features including thickness information and distance from center of mass.

The waist is detected by determining the minor axis of the ovoid shape of the animal after having the tail removed from consideration.

The portion of the body in front of the waist towards the head is called the fore body and the portion of the body aft of the waist towards the tail is called the hind body.

Using these identified points and segments, various parameters such as the orientation, heading direction, turning angle, proximity to other objects or zone boundaries, etc. are obtained.

IV. Behavior Detection Methodology

Each behavior can be modeled as a set of rules or conditions that must be satisfied. The rules or conditions can be formulated using any of the available features or parameters including position and shape of specific body parts with or without respect to other objects, motion characteristics of the entire mouse body or individual body parts, etc. In the descriptions below, all such rules or conditions that are required to derive the specific modeling of the behavior are stated. The behavior descriptions follow:

A. Freeze

Freezing behavior is determined by the absence of movement of rodent body for a brief period of time. Freezing behavior is primarily used in conditioning-fear experiments where auditory tones or electric shock is administered to the animal to cause fear leading to freezing.

B. Sniff at Objects

Sniffing behavior is determined by the touching of the mouth of the rodent body against another defined object, or animal. A zone or area is calibrated to represent this target object or animal, and any encroachment or contact of the head/mouth of the rodent body against or into this target zone is detected as a sniff.

C. Locomote

Locomotion behavior is defined as the movement behavior of the rodent around the cage or arena. Locomotion behavior is best viewed from the top thereby allowing accurate measurements of the total distance traveled, speed, acceleration, heading direction, turning angle, and distance to a specific target.

D. Stretch and Attend

Stretch and Attend behavior is determined by the purposeful extension of the head portion of the rodent body forward and a subsequent retraction of the head while the hind part of the rodent body remains stationary, when viewed from the top. The extension of the head may involve bending it to the side.

E. Head Dip

Head Dipping behavior is determined by the downward movement of the head of the animal over a ledge or a platform, as if to look below. This can be either intentional or unintentional.

F. Transgress from One Area to Another

Transgression behavior is detected by the movement of a portion of, or the entire body of the rodent across from one defined zone or area into another defined zone or area. With this behavior, exit and entrance measures with respect to a zone can be calculated.

V. Behavior Identification

Using the feature data assigned for each of the frames in the video clip, the approach is to determine those behaviors and events as defined in the previous step. This process will be accomplished in real-time so that immediate results will be reported to investigators or stored in a database. One approach is to use a rule-based analysis procedure by which various features are analyzed and if these features fit certain criteria then, that particular behavior or event is detected. For example, "when the mouth touches a object in an object recognition paradigm and remains in contact for a minimum duration of time and then, releases contact with that object and remains out of contact for a certain minimum duration of time, that episode is called "Sniffing".

In summary, when a new video clip is analyzed, the system of the present invention first obtains the video image background and uses it to identify the foreground objects. Then, features are extracted from the foreground objects and various important feature points and segments on the animal are identified. This set of features is passed to a behavior identification system module that identifies the final set of behaviors or events for the video clip. The image resolution of the system that has been obtained and the accuracy of identification of the behaviors attempted so far have been very good and resulted in an effective automated video image object recognition and behavior characterization system.

The invention may identify some abnormal behavior by using video image information (for example, stored in memory) of known abnormal animals to build a video profile for that behavior. Further, abnormalities may also result from an increase in any particular type of normal behavior. Detection of such new abnormal behaviors may be achieved by the present invention detecting, for example, segments of behavior that do not fit the standard profile. The standard profile may be developed for a particular strain of mouse whereas detection of abnormal amounts of a normal behavior can be detected by comparison to the statistical properties of the standard profile. Thus, the automated analysis of the present invention may be used to build a profile of the behaviors, their amount, duration, and daily cycle for each animal, for example each commonly used strain of mice. A plurality of such profiles may be stored in, for example, a database in a data memory of the computer. One or more of these profiles may then be compared to a mouse in question and difference from the profile expressed quantitatively.

The techniques developed with the present invention for automation of the categorization and quantification of all mouse behaviors is a powerful tool for detecting phenotypic effects of gene manipulations in mice. As previously discussed, this technology is extendable to other behavior studies of animals and humans, as well as surveillance purposes. In any case, the present invention has proven to be a significant achievement in creating an automated system and methods for automated accurate identification, tracking and behavior categorization of an object whose image is captured in a video image.

In another preferred embodiment of the invention, there are multiple cameras taking video images of experiment apparatus that contain animals. There is at least one apparatus, but, as many as the computer computing power allows, say four (4) or sixteen (16) or even more, can be analyzed. See FIG. 5. Each apparatus 510 contains at least one animal or multiple animals. The single or multiple cameras 505 may be taking video from different points of views such as one taking video images from the side of the apparatus, or one taking video images from the top of the apparatus. These apparatus can be home cage, open field cage, water maze device, T-maze device, Y-maze device, radial arm maze device, zero maze device, elevated plus maze device, or other experiment devices. The invention can also be applied to various experimental paradigms such as object recognition, and conditioned fear freezing experiments. When video images are taken of multiple apparatuses and devices containing one or multiple animals, and are analyzed for identifying these animals' behaviors, high throughput screening is achieved. When video images taken from different points of views, for example, one from the top view and another from the side view, are combined to identify animal's behaviors, integrated analysis is achieved.

Figure 3:
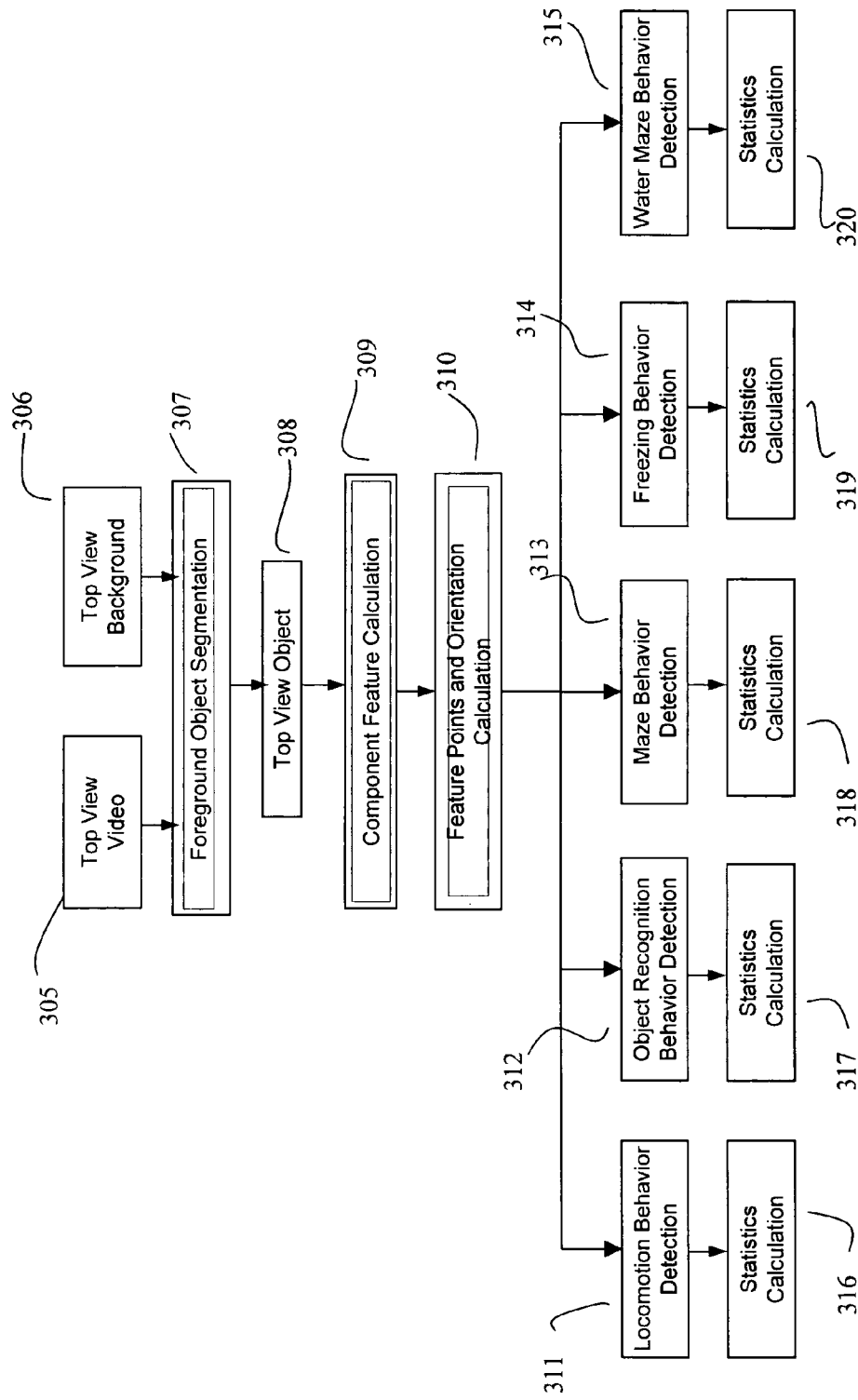
FIG. 3 is a flow chart of a method of automatic video analysis for animal identification and characterization from video shot from the top, according to another embodiment of the present invention.
Figure 4:
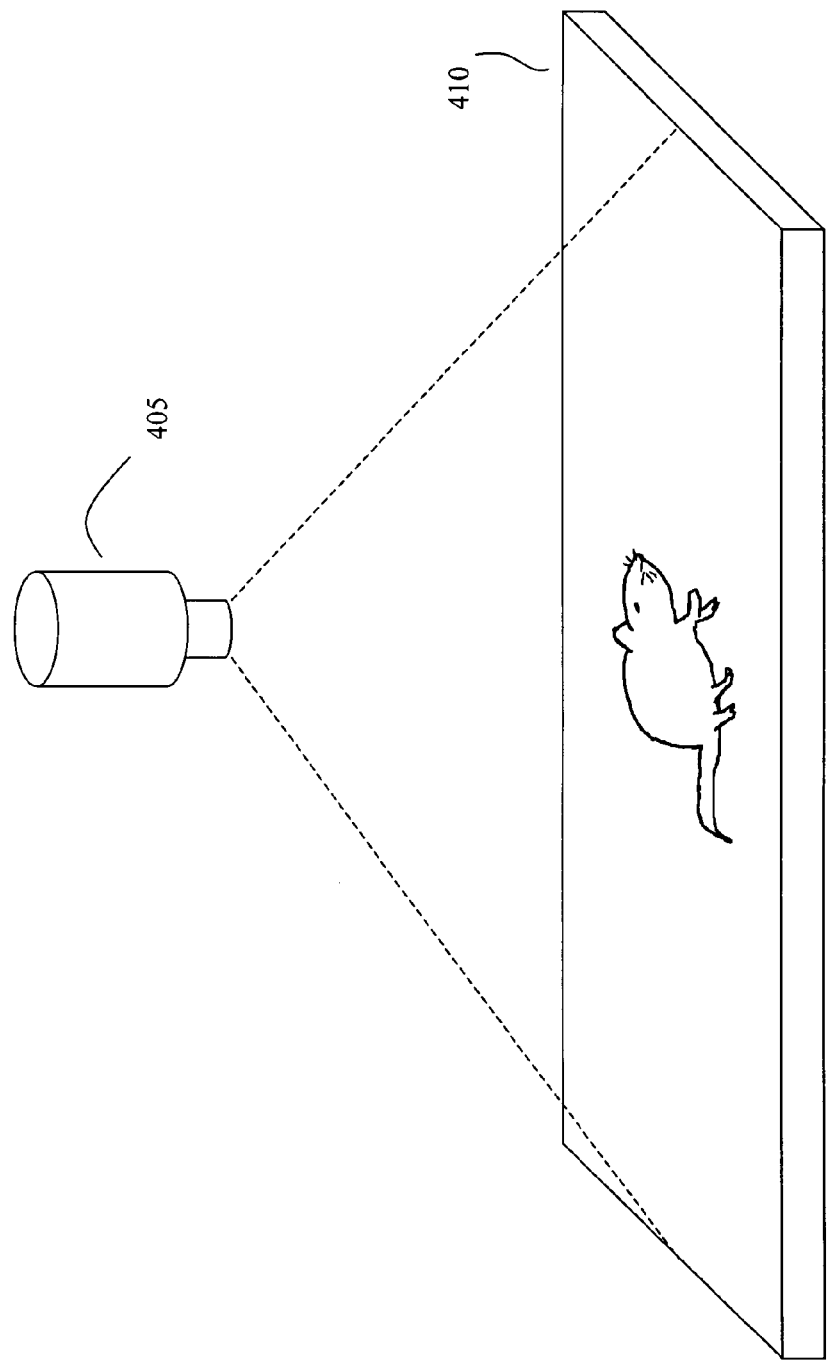
FIG. 4 shows an embodiment of the invention where video is captured from the top.

FIG. 3 is a flowchart of method steps for automatic video analysis for object recognition and characterization, according to one embodiment of the invention. In step 305, top view video of an animal in a behavioral analysis apparatus is obtained. In step 306, top view background video is obtained of the behavioral analysis apparatus. In step 307, the foreground object images (animal) are segmented and in step 308 the foreground object (animal) is identified. In step 309 component features are calculated and in step 310 feature points (body parts) of the animal are identified.

Figure 5:
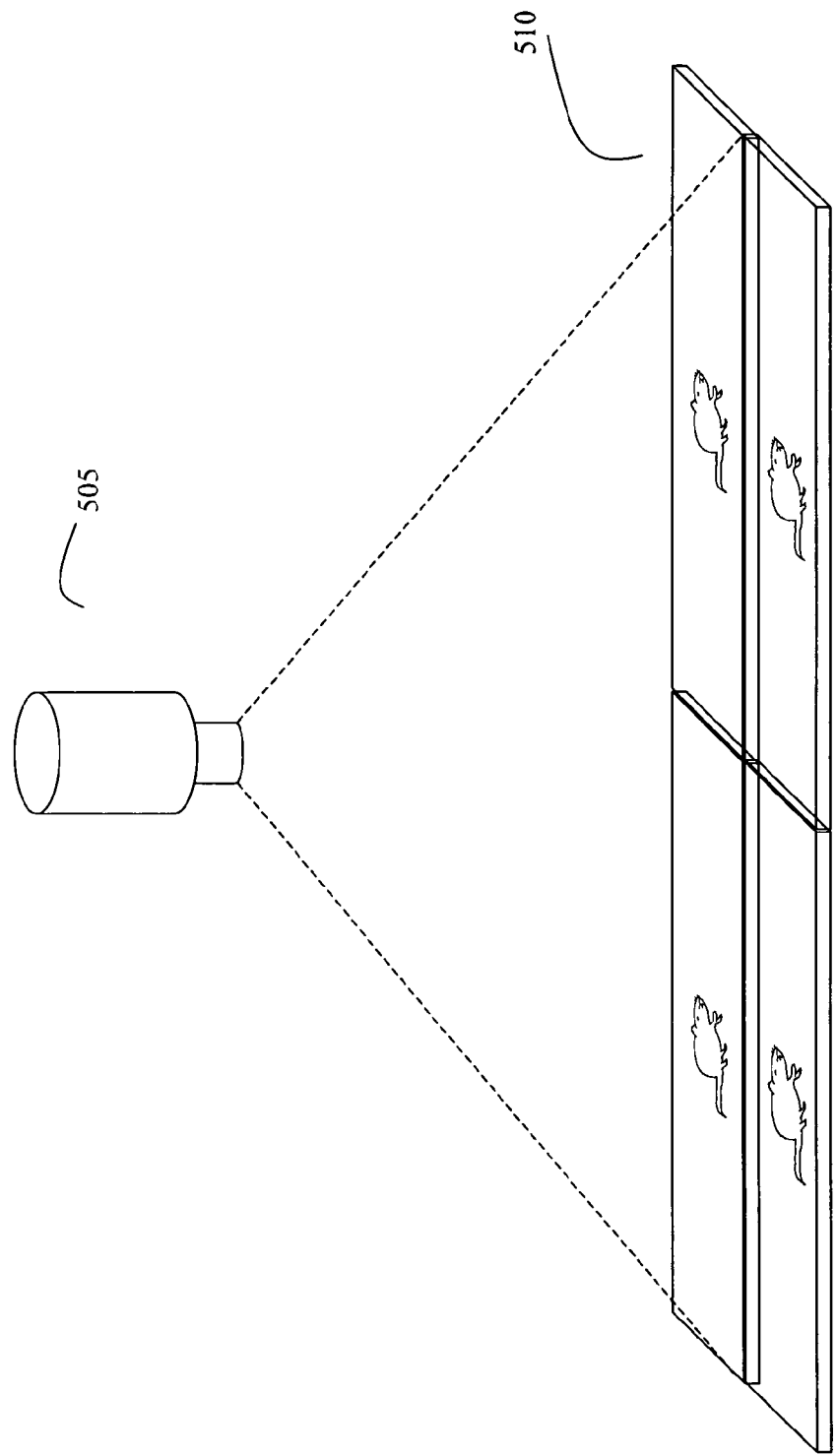
FIG. 5 shows another embodiment of the invention, a top-view based open field locomotion analysis system. Multiple arenas can be analyzed at the same time.

A variation of the present invention is directed to automatically determining locomotion behavior of mice or rats in an open field 311. Once the animal is identified as a foreground object 308 as discussed above, the body parts of the animal such as head and tail, and hind limbs and forelimbs, and center of mass, are identified 310. The traces of the path of the movements of the animal's center of mass in the open field under observation is recorded, its instant and average speed of movements and distance traveled are calculated, its instant and cumulative body turning angles are analyzed 311. In addition, events like turning ratio (ratio of path length over number of turns, where number of turns is counted when the animal makes a turn larger than 80 degrees when the animal travels one body length); proximity score (calculated by determining the distance of the animal from the goal during each second of the trial and is used as a measure of deviation from the ideal path to the platform once an animal is placed in the cage); heading errors (defined as an instance of moving away from a target); and animal staying in a specific zone inside the field, are recorded 316. Then a visualization process will further analyze the result of the path trace recorded to generate variety of statistic results. Visualization process allows users to use graphic drawing tools to define any number of zones of any shape in the open field as needed. The system provides a graphic tool that allows users to define the field of any shape. An example apparatus is shown in FIG. 5, where a camera 505, placed directly above the arenas 510, captures video from the top. A plurality of the arenas may be used and their video captured using a single camera or multiple cameras to achieve high-throughput analysis. The locomotion or movement behavior of the animal in each arena is analyzed.

Figure 7:
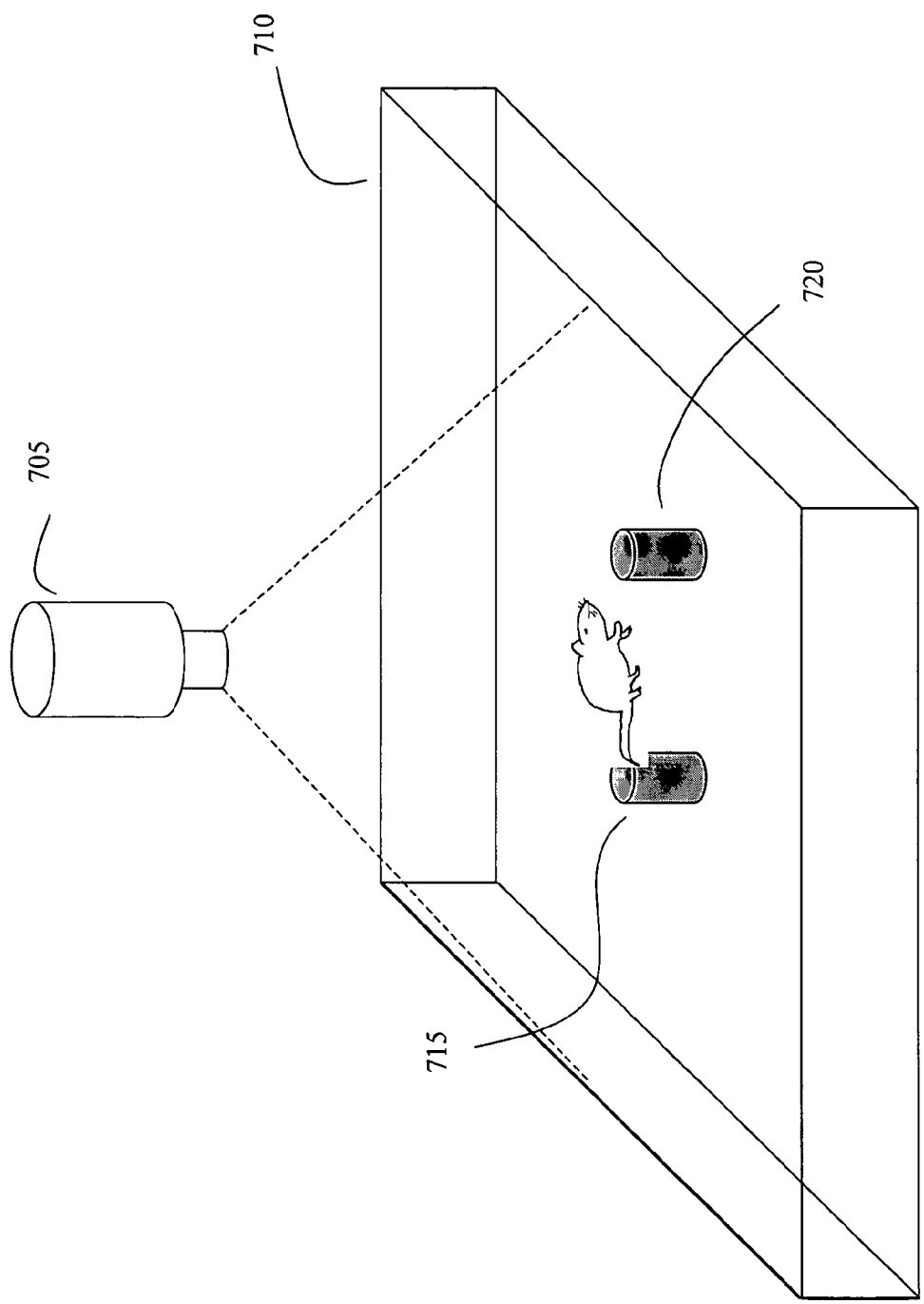
FIG. 7 shows another embodiment of the invention, a top-view based object recognition behavior analysis system. A plurality of objects is placed in the arena and sniffing behavior of the animal on the objects is detected. Multiple arenas can be analyzed at the same time.

Another variation of the present invention is directed to automatically determining the object recognition activity 312. Graphic tools are provided to allow users to define objects in the scene. Once the animal is identified as a foreground object 308 as discussed above, the body parts of the animal such as head and tail and hind limbs and forelimbs, and center of mass are identified 310. The traces of the path of the movements of the animal's center of mass are recorded. The distances of the animal's head to any of the objects in the scene are calculated and when the distance to an object is less than a user-defined amount, the animal is counted as animal's sniffing at the object and is said to be exploring that object 312. Statistics about these exploring events are generated and exported 317. An example apparatus is shown in FIG. 7, where a camera 705, placed directly above the arena 710, capture video from the top.

A plurality of objects, in this case two objects 715, 720 are placed in the arena and the exploratory or sniffing behaviors of the animal on these objects are analyzed.

Figure 8:
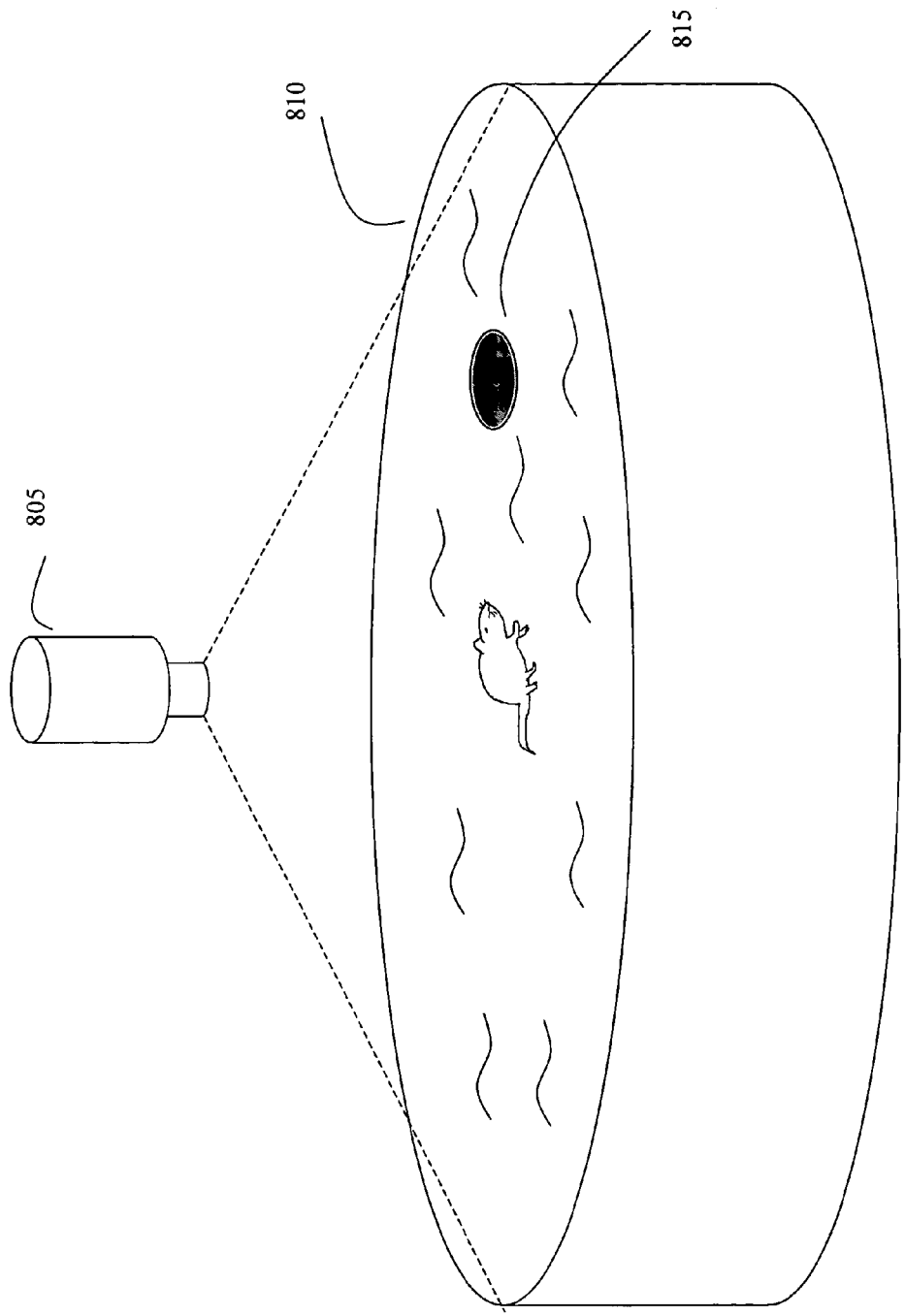
FIG. 8 shows another embodiment of the invention, a top-view based water maze behavior analysis system. The platform is the target for the animal.

Another variation of the previous embodiments is particularly applicable to the study and analysis of mice or rats in their spatial learning and memory. This third variation of the present invention is directed towards automatically determining the behaviors of mice or rats in a water maze experiment environment 315. Graphic tools are provided to allow users to define the maze and platforms. Once the animal is identified as a foreground object 308 as discussed above, the body parts of the animal such as head and tail and hind limbs and forelimbs, and center of mass are identified 310. The traces of the path of the movements of the animal's center of mass are recorded. The latency (the time period the animal spent in swimming in the water before landing at the platform) is measured; its instant and average speed of movements and distance traveled are calculated; its instant and cumulative body turning angles are analyzed 315. In addition, events like turning ratio (ratio of path length over number of turns, where number of turns is counted when the animal makes a turn larger than 90 degrees when the animal travels one body length); proximity score (calculated by determining the distance of the animal from the goal (platform) during each second of the trial and is used as a measure of deviation from the ideal path to the platform once an animal is placed in the water); heading errors (defined as an instance of swimming away from the VISIBLE platform); and animal staying in a specific zone inside the maze, are recorded 320. Then a visualization process will further analyze the result of the path trace recorded to generate variety of statistic results. Visualization process allows users to use graphic drawing tools to define any number of zones of any shape in the open field as needed. The system provides a graphic tool that allows users to define the field of any shape. An example apparatus is shown in FIG. 8, where a camera 805, placed directly above the water tank 810, captures video from the top and the movement behavior of the animal inside the water tank and its relationship with the target platform 815 is analyzed.

Figure 6:
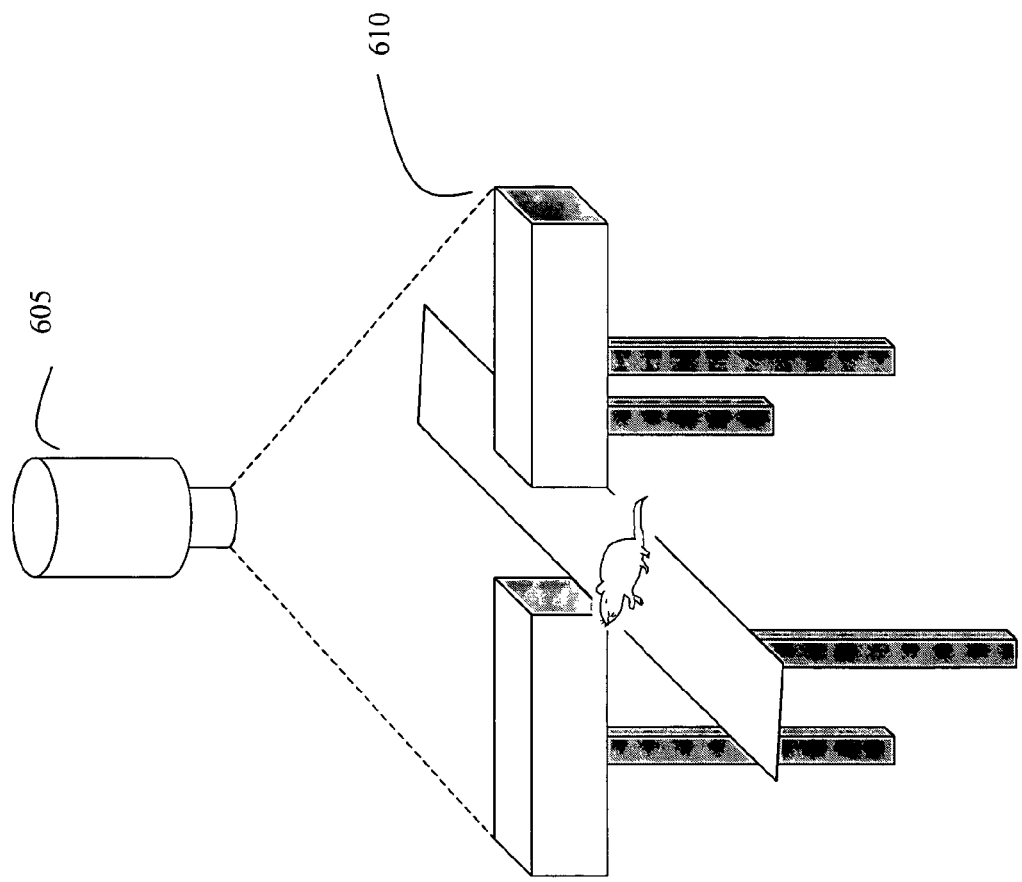
FIG. 6 shows another embodiment of the invention, a top-view based maze behavior analysis system. An elevated plus maze is shown, but other types of mazes such as zero maze, T-maze, Y-maze, radial arm maze can be used.

Another variation of the previous embodiments is particularly applicable to the study and analysis of mice or rats in their spatial learning and memory and anxiety. This fourth variation of the present invention is directed towards automatically determining the behaviors of mice or rats in a variety of maze apparatus 313. Graphic tools are provided to define specific maze apparatus, such as T-maze, Y-maze, radial arm maze, zero maze, elevated plus maze, and etc. Once the animal is identified as a foreground object 308 as discussed above, the body parts of the animal such as head and tail and hind limbs and forelimbs, and center of mass are identified 310. The traces of the path of the movements of the animal's center of mass are recorded. More importantly, the animal's behaviors related to every arm in the maze, such as time spent in each arm, the number of times entering and exiting an arm, are found 313. Besides, animal's instant and average speed of movements and distance traveled are calculated; its instant and cumulative body turning angles are analyzed 318. In addition, events such as animal partial incursions into particular arm (for example, the animal might maintain its hind quarters in a closed arm while poking its nose into an open arm); Stretch-Attend Behavior; Head-Dipping behavior; and Supported Rearing, are detected 313. An example apparatus is shown in FIG. 6 where an elevated plus maze 610 is used to analyze the behavior of the animal. A camera 605, placed directly above, capture video from the top and analyzes the movement behaviors in various arms or areas of the maze.

Figure 9:
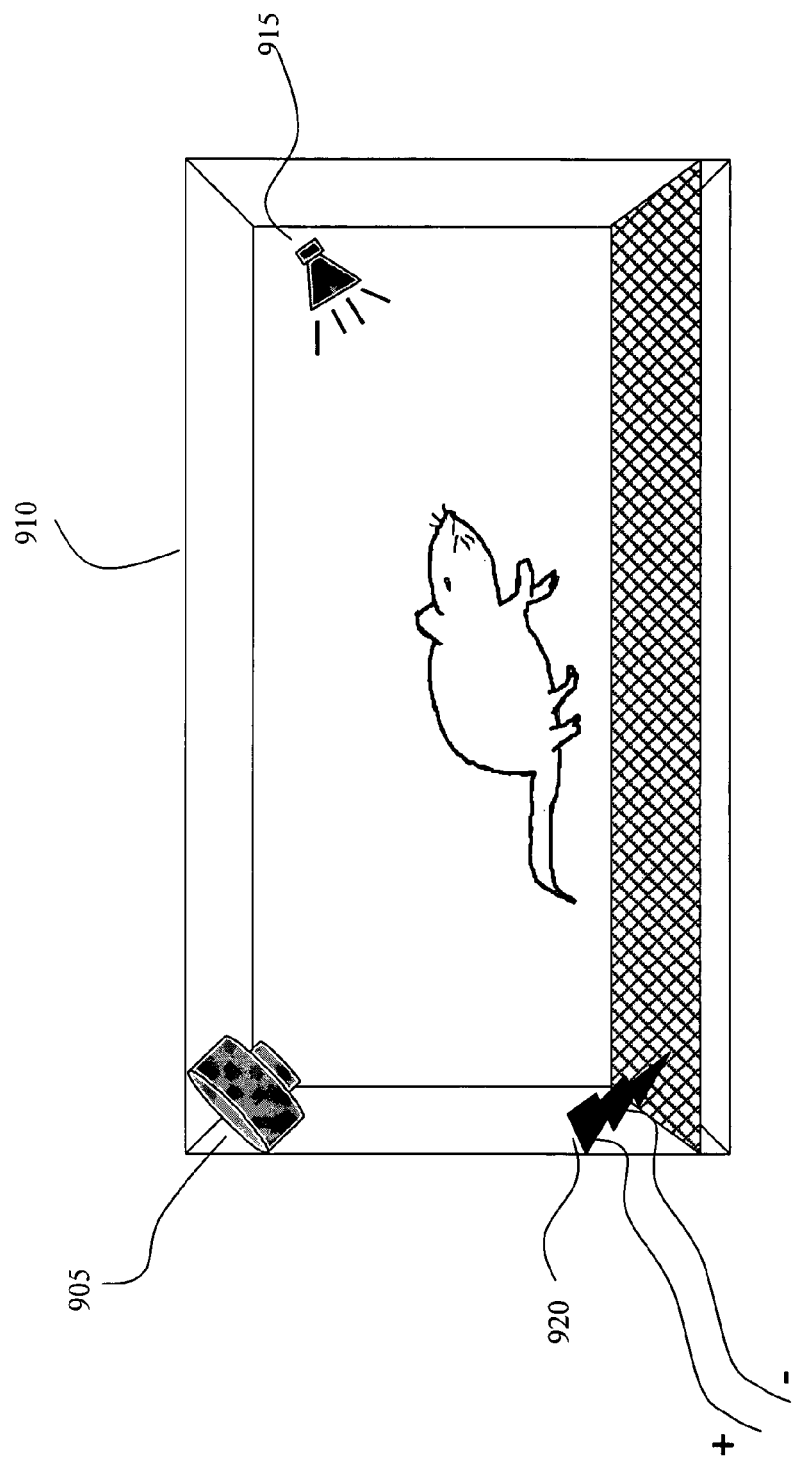
FIG. 9 shows another embodiment of the invention, a freezing behavior analysis system. The animal is placed inside a chamber where stimuli such as electric shock or auditory tones are used and the resulting behavior after the stimuli are observed.

Fifth variation of the present invention is directed to automatically determining the freezing behaviors of mice or rats in a cued or conditioned fear tests 314. Graphic tools are provided. Graphic tools are provided to define the area within which animal activity is measured. Differences between neighboring frames are compared pixel-by-pixel in terms of their intensity and color intensity. These differences are used to calculate the motion of the animal from frame-to-frame because motion in the area is caused by movements of the animal. The values of these differences indicate if the animal is moving or freezing 314. An example apparatus is shown is FIG. 9. The camera 905 maybe placed inside or outside the chamber 910. The animal is placed inside the chamber and stimuli in the form of auditory tones 915 or electric shock 920 is presented and their behavioral effects following the stimuli are analyzed.

The systematically developed definitions of mouse behaviors that are detectable by the automated analysis according to the present invention makes precise and quantitative analysis of the entire mouse behavior repertoire possible for the first time. The various computer algorithms included in the invention for automating behavior analysis based on the behavior definitions ensure accurate and efficient identification of mouse behaviors. In addition, the digital video analysis techniques of the present invention improves analysis of behavior by leading to: (1) decreased variance due to non-disturbed observation of the animal; (2) increased experiment sensitivity due to the greater number of behaviors sampled over a much longer time span than ever before possible; and (3) the potential to be applied to all common normative behavior patterns, capability to assess subtle behavioral states, and detection of changes of behavior patterns in addition to individual behaviors.

Although particular embodiments of the present invention have been shown and described, it will be understood that it is not intended to limit the invention to the preferred or disclosed embodiments, and it will be obvious to those skilled in the art that various changes and modifications may be made without departing from the spirit and scope of the present invention. Thus, the invention is intended to cover alternatives, modifications, and equivalents, which may be included within the spirit and scope of the invention as defined by the claims.

For example, the present invention may also include audio analysis and/or multiple camera analysis. The video image analysis may be augmented with audio analysis since audio is typically included with most video systems today. As such, audio may be an additional variable used to determine and classify a particular objects behavior. Further, in another variation, the analysis may be expanded to video image analysis of multiple objects, for example mice, and their social interaction with one another. In a still further variation, the system may include multiple cameras providing one or more planes of view of an object to be analyzed. In an even further variation, the camera may be located in remote locations and the video images sent via the Internet for analysis by a server at another site. In fact, the standard object behavior data and/or database may be housed in a remote location and the data files may be downloaded to a stand alone analysis system via the Internet, in accordance with the present invention. These additional features/functions add versatility to the present invention and may improve the behavior characterization capabilities of the present invention to thereby achieve object behavior categorization which is nearly perfect to that of a human observer for a broad spectrum of applications.

All publications, patents, and patent applications cited herein are hereby incorporated by reference in their entirety for all purposes.

What is claimed is:

1. A method for characterizing animal behavior, comprising:
    segregating images of an animal from video images of the animal in a behavioral analysis apparatus, wherein the video images are taken only from a top view;
    identifying at least one body part of the animal based on the images taken from a top view;
    identifying a center of mass of the animal based on the images taken from a top view; and
    characterizing behavior of the animal using the at least one body part and the center of mass of the animal.

2. The method of claim 1, wherein segregating images of an animal from video images includes subtracting a background image from a video image containing an image of an animal.

3. The method of claim 1, wherein characterizing behavior of the animal includes comparing a location of the at least one body part of the animal and a location of the center of mass of the animal to pre-trained behavior models.

4. The method of claim 1, wherein characterizing behavior of the animal includes comparing a location of the at least one body part of the animal and a location of the center of mass of the animal to predefined rules.

5. The method of claim 1, wherein characterizing the behavior of the animal includes determining the location of the at least one body part of the animal in relation to a user-defined virtual zone.

6. The method of claim 1, wherein characterizing the behavior of the animal includes determining the location of the center of mass of the animal in relation to a user-defined virtual zone.

7. The method of claim 1, wherein the at least one body part is a head.

8. The method of claim 1, wherein the at least one body part is a tail.

9. The method of claim 1, wherein the at least one body part is a waist.

10. The method of claim 1, wherein the at least one body part is a fore body.

11. The method of claim 1, wherein the at least one body part is a hind body.

12. The method of claim 1, wherein the behavior analysis apparatus is an open field apparatus.

13. The method of claim 1, wherein the behavior analysis apparatus is a maze apparatus.

14. The method of claim 1, wherein the behavior analysis apparatus includes recognition objects.

15. The method of claim 1, wherein the behavior analysis apparatus includes a fear chamber.

16. A method for characterizing animal behavior, comprising:
    segregating images of an animal from video images of the animal in a behavioral analysis apparatus, wherein the video images are taken only from a top view;
    identifying at least one body part of the animal based on the images taken from a top view;
    identifying a center of mass of the animal based on the images taken from a top view; and
    detecting behavioral events of the animal using the at least one body part and the center of mass of the animal.

17. The method of claim 16, wherein detecting behavior events includes comparing a location of the at least one body part of the animal and a location of the center of mass of the animal to pre-trained behavior models.

18. The method of claim 16, wherein detecting behavioral events includes comparing a location of the at least one body part of the animal and a location of the center of mass of the animal to predefined rules.

19. The method of claim 16, wherein detecting behavioral events includes detecting a turning ratio of the animal by taking a ratio of a path length traveled over a number of turns, wherein a turn is counted when the animal makes a turn larger than ninety degrees when the animal travels one body length.

20. The method of claim 16, wherein detecting behavioral events includes detecting sniffing behavior of the animal by detecting when the animal's nose is in contact with a recognition object in the behavioral analysis apparatus.

21. The method of claim 16, wherein detecting behavioral events includes detecting stretch-and-attend by detecting the animal's approach to an object with fore body stretched and then lowered, followed by retraction of the fore body.

22. The method of claim 16, wherein detecting behavioral events includes detecting stay-across-areas by detecting the animal's partial incursions into a zone of the behavioral analysis apparatus.

23. The method of claim 16, wherein detecting behavioral events includes detecting head dipping by detecting the animal's exploratory movement of its head over an edge of the behavioral analysis apparatus.

24. The method of claim 16, wherein detecting behavioral events includes detecting freezing by detecting an absence of movement of the animal's body for a period of time.

25. The method of claim 16, wherein detecting behavioral events includes detecting locomoting by detecting movement of the animal within the behavioral analysis apparatus.

26. The method of claim 16, wherein detecting behavioral events includes detecting transgressing behavior by detecting movement of the animal from a defined zone within the behavioral analysis apparatus to another defined zone within the behavioral analysis apparatus.

27. The method of claim 16, wherein detecting behavioral events includes calculating a proximity score by determining a distance of the animal from a goal at predetermined time intervals.

28. The method of claim 16, wherein detecting behavioral events includes determining heading errors by detecting when the animal is moving away from a goal.

29. The method of claim 16, wherein the at least one body part is a head.

30. The method of claim 16, wherein the at least one body part is a tail.

31. The method of claim 16, wherein the at least one body part is a waist.

32. The method of claim 16, wherein the at least one body part is a fore body.

33. The method of claim 16, wherein the at least one body part is a hind body.

34. A non-transitory computer-readable medium including instructions for performing:
   segregating images of an animal from video images of the animal in a behavioral analysis apparatus, wherein the video images are taken only from a top view;
   identifying at least one body part of the animal based on the images taken from a top view;
   identifying a center of mass of the animal based on the images taken from a top view; and
   characterizing behavior of the animal using the at least one body part and the center of mass of the animal.

35. The computer-readable medium of claim 34, wherein characterizing behavior of the animal includes comparing a location of the at least one body part of the animal and a location of the center of mass of the animal to pre-trained behavior models.

36. The computer-readable medium of claim 34, wherein characterizing behavior of the animal includes comparing a location of the at least one body part of the animal and a location of the center of mass of the animal to predefined rules.

37. The computer-readable medium of claim 34, wherein the at least one body part is a head.

38. The computer-readable medium of claim 34, wherein the at least one body part is a tail.

39. The computer-readable medium of claim 34, wherein the at least one body part is a waist.

40. The computer-readable medium of claim 34, wherein the at least one body part is a fore body.

41. The computer-readable medium of claim 34, wherein the at least one body part is a hind body.

* * * * *